(12) United States Patent
Hyde et al.

(10) Patent No.: US 10,188,316 B2
(45) Date of Patent: Jan. 29, 2019

(54) SYSTEMS AND METHODS FOR MODULAR INTRALUMINAL DEVICE POWER TRANSFER

(71) Applicant: Elwha LLC, Bellevue, WA (US)

(72) Inventors: Roderick A. Hyde, Redmond, WA (US); Jordin T. Kare, San Jose, CA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 211 days.

(21) Appl. No.: 15/051,126

(22) Filed: Feb. 23, 2016

(65) Prior Publication Data

US 2017/0238840 A1    Aug. 24, 2017

(51) Int. Cl.
*A61B 5/07*    (2006.01)
*A61B 5/00*    (2006.01)
(Continued)

(52) U.S. Cl.
CPC ............ *A61B 5/073* (2013.01); *A61B 5/0084* (2013.01); *A61B 5/01* (2013.01); *A61B 5/05* (2013.01); *A61B 5/062* (2013.01); *A61B 5/1473* (2013.01); *A61B 5/6861* (2013.01); *A61B 5/6882* (2013.01); *A61B 5/6885* (2013.01); *H02J 7/025* (2013.01); *H02J 50/00* (2016.02); *A61B 5/036* (2013.01); *A61B 5/103* (2013.01);
(Continued)

(58) Field of Classification Search
None
See application file for complete search history.

(56) References Cited

U.S. PATENT DOCUMENTS 7,118,531 B2 * 10/2006 Krill ...................... A61B 1/041
600/109
7,473,218 B2 * 1/2009 Segawa ................ A61B 1/0011
348/340

(Continued)

OTHER PUBLICATIONS

Pan, Guobing; Wang, Litong; "Swallowable Wireless Capsule Endoscopy: Progress and Technical Challenges", vol. 2012, Article ID 841691, 9 pp., Oct. 10, 2011, Gastroenterology Research and Practice.

(Continued)

*Primary Examiner* — Meredith Weare
(74) *Attorney, Agent, or Firm* — Daniel J. Honz; Advent, LLP

(57) ABSTRACT

Systems and methods are described for providing power transfer between modular intraluminal devices. A system embodiment includes, but is not limited to, a first intraluminal device and a second intraluminal device; the first intraluminal device including a body structure, a sensor, a processor, a data transmitter, and an energy storage module configured to power at least one of the sensor, the processor, or the data transmitter; the second intraluminal device including a second body structure, an energy storage device, and a docking structure, where the energy storage device is configured to transfer energy when the first intraluminal device and the second intraluminal device are coupled via the docking structure, the docking structure further configured to automatically decouple the first intraluminal device and the second intraluminal device subsequent to transfer of the energy.

14 Claims, 19 Drawing Sheets

(51) Int. Cl.
    *A61B 5/1473*     (2006.01)
    *A61B 5/05*     (2006.01)
    *A61B 5/06*     (2006.01)
    *A61B 5/01*     (2006.01)
    *H02J 7/02*     (2016.01)
    *H02J 50/00*     (2016.01)
    *A61B 5/03*     (2006.01)
    *A61B 5/103*     (2006.01)
    *A61B 5/20*     (2006.01)

(52) U.S. Cl.
    CPC ......... *A61B 5/20* (2013.01); *A61B 2560/0219* (2013.01); *A61B 2560/0456* (2013.01); *A61B 2562/0204* (2013.01)

(56) References Cited

U.S. PATENT DOCUMENTS

| | | | |
|---|---|---|---|
| 7,678,043 B2* | 3/2010 | Gilad | A61B 1/00156 600/109 |
| 8,142,350 B2* | 3/2012 | Frisch | A61B 1/00105 600/160 |
| 8,246,537 B2* | 8/2012 | Fujimori | A61B 1/00029 600/160 |
| 9,511,211 B2* | 12/2016 | Tange | A61B 5/4839 |
| 2003/0065250 A1 | 4/2003 | Chiel et al. | |
| 2004/0027459 A1* | 2/2004 | Segawa | A61B 1/0011 348/207.99 |
| 2004/0122315 A1* | 6/2004 | Krill | A61B 1/041 600/437 |
| 2007/0010709 A1* | 1/2007 | Reinschke | A61B 1/00082 600/116 |
| 2007/0156015 A1* | 7/2007 | Gilad | A61B 1/00156 600/102 |
| 2007/0282164 A1* | 12/2007 | Frisch | A61B 1/00105 600/109 |
| 2008/0114204 A1* | 5/2008 | Fujimori | A61B 1/00029 600/130 |
| 2008/0194912 A1* | 8/2008 | Trovato | A61B 1/00055 600/118 |
| 2011/0202070 A1 | 8/2011 | Dario et al. | |
| 2015/0045658 A1* | 2/2015 | Tange | A61B 5/073 600/424 |

OTHER PUBLICATIONS

Basar, MD Rubel; Ahmad, Mohd Yazed; Cho, Jongman; Ibrahim, Fatimah; "Application of Wireless Power Transmission Systems in Wireless Capsule Endoscopy: An Overview", pp. 10929-10951, Jun. 19, 2014, Sensors 2014, 14.

Lazzi, Gianluca; "Thermal Effects of Bioimplants", pp. 75-81, Sep.-Oct. 2005, IEEE Engineering in Medicine and Biology Magazine.

Carta, R.; Sfakiotakis, M.; Pateromichelakis, N.; Thone, J.; Tsakiris, D.P.; Puers, R.; "A Multi-Coil Inductive Powering System for an Endoscopic Capsule with Vibratory Actuation", 2011, Science Direct.

Adeeb, M.A.; Islam, A.B.; Haider, M.R.; Tulip, F.S.; Ericson, M.N.; Islam, S.K.; "An Inductive Link-Based Wireless Power Transfer System for Biomedical Applications", vol. 2012, Article ID 879294, 11 pp., Mar. 5, 2012, Active and Passive Electronic Components.

Andra, W.; d'Ambly, C.G.; Hergt, R.; Hilger, I.; Kaiser, W.A.; "Temperature distribution as function of time around a small spherical heat source of local magnetic hyperthermia", pp. 197-203, Journal of Magnetism and Magnetic Materials 194 (1999).

http://www.cdc.gov/mmwr/preview/mmwrhtml/mm5548a3.htm.

Harada, Kanako; Susilo, Ekawahyu; Watanabe, Takao; Kawamura, Kazuya; Fujie, Masakatsu G.; Menciassi, Arianna; Dario, Paolo; "Modular Robotic Approach in Surgical Applications—Wireless Robotic Modules and a Reconfigurable Master Device for Endoluminal Surgery", Intechopen.

Olivo, Jacopo; Ghoreishizadeh, Sara S.; Carrara, Sandro; Giovanni, Micheli De; "Electronic Implants: Power Delivery and Management", Integrated Systems Laboratory—EPFL.

Harada, Kanako; Oetomo, Denny; Susilo, Ekawahyu; Menciassi, Arianna; Daney, David; Merlet, Jean-Pierre; Dario, Paolo; "A reconfigurable modular robotic endoluminal surgical system: vision and preliminary results", vol. 28, pp. 171-183, 2010, Robotica.

Yoo, Seung-Schik; Rama, Suraj; Szewczyk, Benjamin; Pui, Jason W.Y.; Lee, Wonhye; Kim, Laehyun; "Endoscopic Capsule Robots Using Reconfigurable Modular Assembly: A Pilot Study", vol. 24, pp. 359-365, Boston University.

Consumer Product Safety Commission, "Final Rule: Safety Standard for Magnet Sets", 2014, pp. 113-129.

* cited by examiner

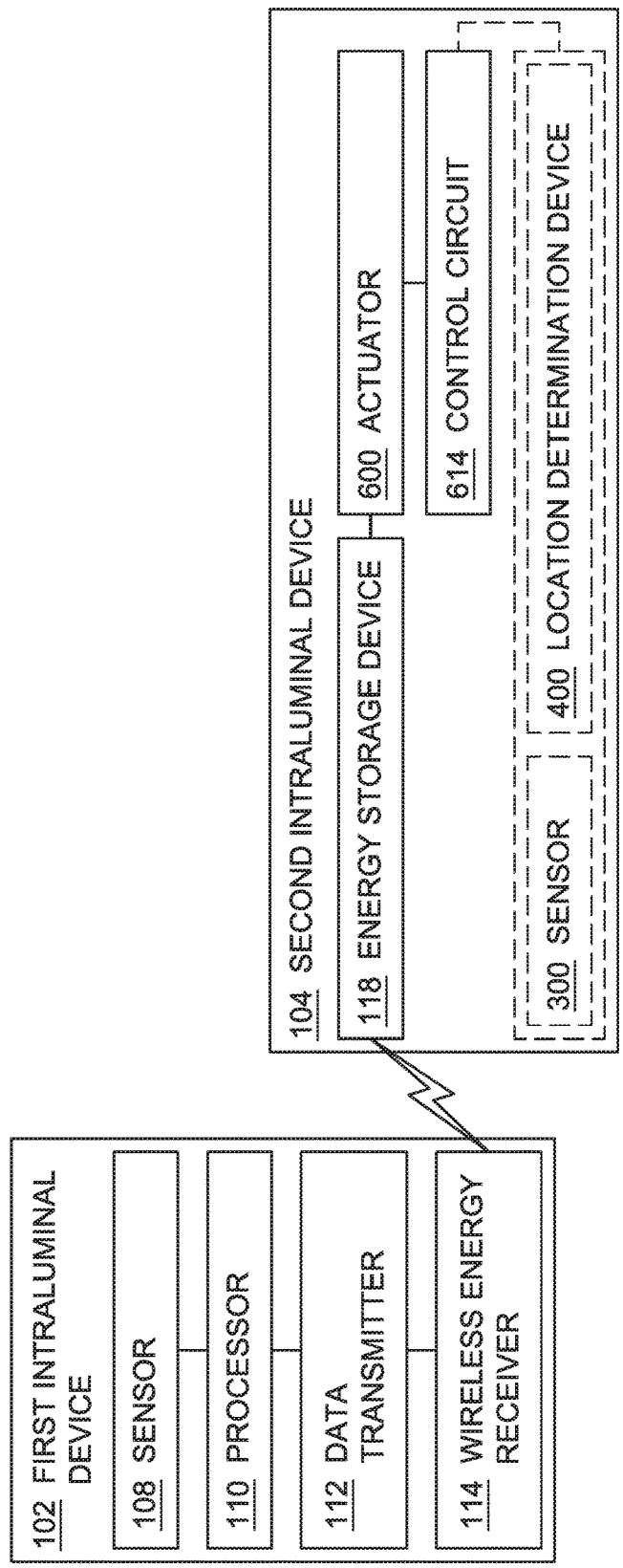

SYSTEMS AND METHODS FOR MODULAR INTRALUMINAL DEVICE POWER TRANSFER

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system includes, but is not limited to, a first intraluminal device and a second intraluminal device; the first intraluminal device including a body structure dimensioned and structured to travel through a biological lumen of a subject; a sensor coupled to the body structure, the sensor oriented to detect at least one characteristic of the biological lumen and to generate one or more sense signals in response thereto; a processor operably coupled to the sensor, the processor configured to receive the one or more sense signals; a data transmitter coupled to the body structure and configured to wirelessly transmit one or more data signals associated with the one or more sense signals responsive to instruction by the processor; and an energy storage module configured to power at least one of the sensor, the processor, or the data transmitter; the second intraluminal device including a second body structure dimensioned and structured to travel through the biological lumen of the subject; an energy storage device coupled to the second body structure, the energy storage device configured to transfer energy stored in the energy storage device to the energy storage module of the first intraluminal device; and a docking structure coupled to the second body structure, the docking structure configured to couple the first intraluminal device with the second intraluminal device, the energy storage device configured to transfer the energy when the first intraluminal device and the second intraluminal device are coupled via the docking structure, the docking structure further configured to automatically decouple the first intraluminal device and the second intraluminal device subsequent to transfer of the energy from the energy storage device of the second intraluminal device to the energy storage module of the first intraluminal device.

In an aspect, a method for intraluminal analysis includes, but is not limited to, introducing a first intraluminal device into a biological lumen of a subject, the first intraluminal device including an energy storage module configured to receive energy originating external to the first intraluminal device to power at least one component of the first intraluminal device; and introducing a second intraluminal device into the biological lumen of the subject, the second intraluminal device including an energy storage device configured to transfer energy stored in the energy storage device to the energy storage module of the first intraluminal device when the first intraluminal device and the second intraluminal device are conditionally coupled within the subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6E is a schematic of an embodiment of a system such as shown in FIG. 1.

DETAILED DESCRIPTION

Figure 1:
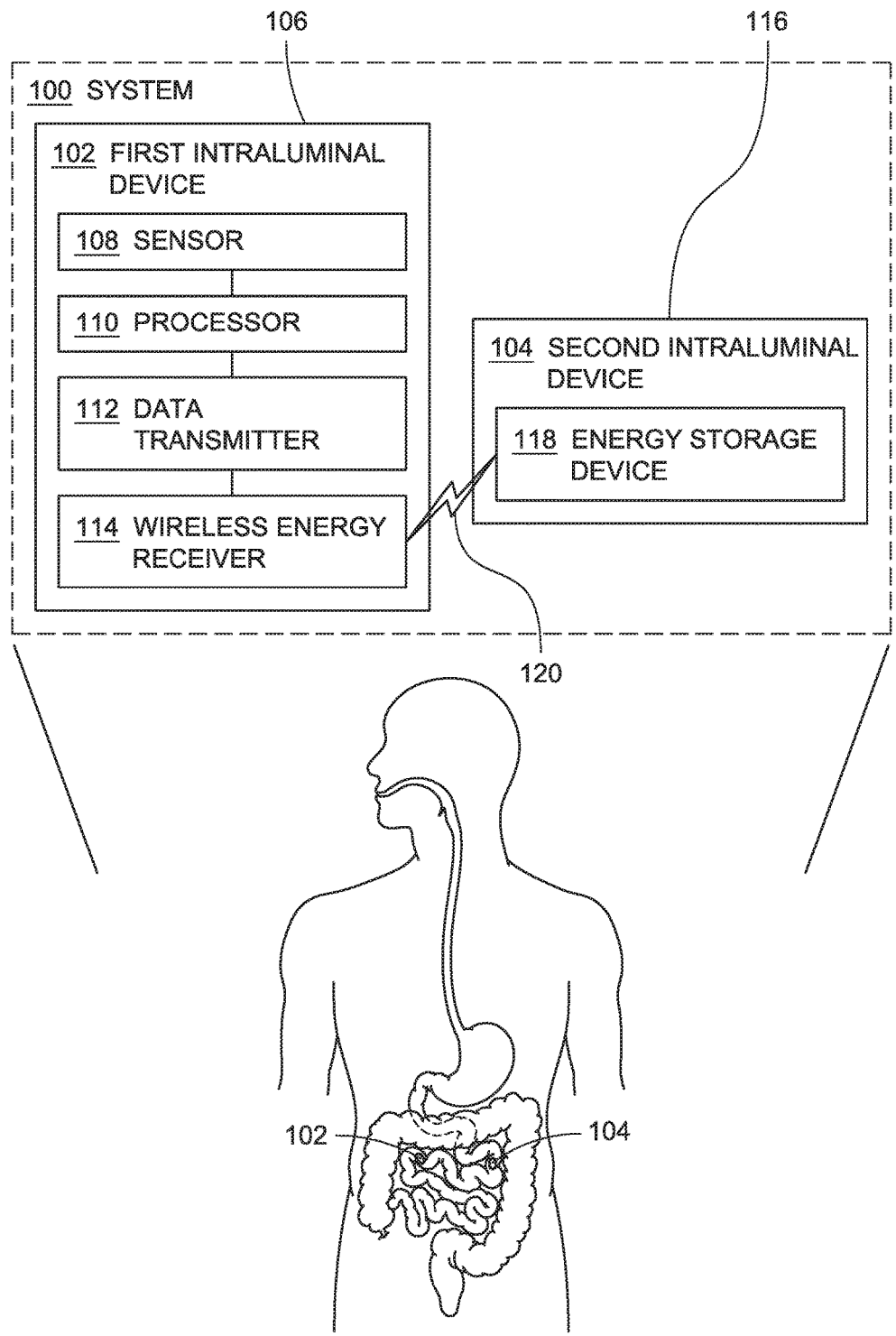
FIG. 1 is a schematic of a system for modular intraluminal device power transfer.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems and methods are described for providing power transfer between modular intraluminal devices when placed within an individual subject, such as within one or more biological lumens. The biological lumens can be associated with any biological lumen network of an individual subject, such as a lumen associated with at least one of a gastrointestinal system, a respiratory system, a cardiovascular system, a nervous system, a urinary system, a reproductive system, a lymphatic system, a biliary system, a glandular system, an auditory system, a visual system, or a nasal system. For instance, medical personnel can employ endoscopy techniques to monitor gastrointestinal health, which may lead to the detection of diseases. Endoscopy allows medical personnel to view the tissue comprising the gastrointestinal tract and to more easily identify problems that may otherwise require extensive testing or go undetected. Wired endoscope devices can be utilized for such diagnostics, however such devices often cannot feasibly reach or monitor the small intestine. This leaves medical personnel to speculate about the health of a patient's overall gastrointestinal tract. In some instances, discomfort or pain may be experienced by patients as a wired endoscope is moved through the body, which can cause intestinal perforation. Wireless capsule endoscopy can be utilized to view the entire gastrointestinal tract, while minimizing pain associated with wired endoscopes. Wireless capsule endoscopy uses a capsule that may be small enough for a patient to ingest and may be powered by local power supplies (e.g., batteries). However, the power supplied from local power supplies may not last long enough for medical personnel to view the entire gastrointestinal tract or to provide other diagnostic or treatment procedures. Also the motion of a capsule endoscope may be dictated by the movement of the gastrointestinal tract, limiting the feasible diagnostic or treatment functionalities. Further, external powering techniques for such wireless capsule endoscopes face challenges associated with transit times, significant distances between power transmitting and receiving coils, unpredictable wireless capsule orientation and motion, and complexity and size requirements associated with receiving coils on the capsule.

The systems and methods described herein can facilitate power transfer between modular intraluminal devices located within a body of an individual subject, wherein the intraluminal devices can provide diagnostic, analytic, and treatment functionalities within a biological lumen, such as to facilitate medical diagnosis of the individual subject by a medical professional or to facilitate treatment of the individual subject by drug delivery, surgical applications, or so forth. In an embodiment, power transfer between modular intraluminal devices is facilitated via control of the movements of one or more of the intraluminal devices, such as to bring one intraluminal device closer to another intraluminal device, to increase or decrease a distance between the intraluminal devices, to control an orientation of one of the intraluminal devices relative to another intraluminal device, or so forth, which can bring the intraluminal devices into and out of position to transfer power from one intraluminal device to another intraluminal device. For example, locomotion of a second intraluminal device introduced to the biological lumen subsequent to introduction of a first intraluminal device can be controlled to bring the second intraluminal device closer to the first intraluminal device, or to adjust an orientation of the second intraluminal device relative to the first intraluminal device. Further, the locomotion of one of the intraluminal devices can be arrested to increase or decrease a distance between intraluminal devices, or to change an orientation of one of the intraluminal devices relative to another intraluminal device, such as by allowing biological conditions (e.g., fluid flow, muscular movement, etc.) or controlled locomotion to influence the non-arrested intraluminal device. The systems can control activation of the power transfer based on proper positioning of the intraluminal devices relative to one another, through identification of the intraluminal devices, through external control, through identification of one or more environmental conditions within the individual subject, or through other activation protocols.

In an embodiment, intraluminal devices include one or more propelling structures, locomotive structures, steering structures, or motion-resistive mechanisms to influence the propulsion, positioning, or orientation of the intraluminal devices to influence power transfer from one intraluminal device to another intraluminal device.

In an embodiment, the systems and methods described herein employ a first intraluminal device including a sensor oriented to detect at least one characteristic of the biological lumen and to generate sense signals. The sensor can include, but is not limited to, an optical device, a physiological sensor, a pH sensor, a pressure sensor, a temperature sensor, a chemical sensor, or a biosensor.

In an embodiment, the systems and methods described herein employ a first intraluminal device including a wireless energy receiver. The first intraluminal device is operably coupled with a second intraluminal device including an energy storage device to wirelessly transfer energy stored in the energy storage device to the wireless energy receiver while the first intraluminal device and the second intraluminal device are positioned within the individual subject. The power transfer can sustain activities and functionality of the first intraluminal device while present in the individual subject. The wireless power transfer can occur via one or more energy transfer protocols including, but not limited to, electromagnetic coupling, microwave coupling, infrared coupling, optical coupling, or acoustic coupling. In an embodiment, the systems and devices described herein can initiate transfer of the power based on an actuator responsive to a timer output, a sensor output (e.g., indicative of a condition within the biological lumen), a power state of the first intraluminal device, or an external communication.

In an embodiment, shown in FIG. 1, a system (or device) 100 is configured to provide wireless power or energy transfer between modular intraluminal devices when the intraluminal devices are positioned within one or more biological lumens of an individual subject (e.g., a human subject, an animal subject). The system 100 includes a first intraluminal device 102 and a second intraluminal device 104, each of which is configured for deployment within one or more biological lumens within the individual subject, such as a lumen of the gastrointestinal tract shown in FIG. 1. While FIG. 1 shows the first intraluminal device 102 and the second intraluminal device 104 within the lumen of the gastrointestinal tract, the system 100 can operate within biological lumens associated with any biological lumen network of an individual subject, such as a lumen associated with at least one of a gastrointestinal system, a respiratory system, a cardiovascular system, a nervous system, a urinary system, a reproductive system, a lymphatic system, a biliary system, a glandular system, an auditory system, a visual system, or a nasal system. For example, embodiments of the systems or devices described herein may be configured for use in (e.g., configured to fit within) a body lumen of an organism including, for example, the respiratory tract, the cardiovascular system (e.g., a blood vessel), a portion of a CSF-space (cerebro-spinal fluid space) of the nervous system (e.g., the spinal canal, the ventricles of the brain, the sub-arachnoid space, etc.), a portion of the urinary tract (for example a ureter), a portion of the lymphatic system, a portion of the abdominal cavity, a portion of the thoracic cavity, a portion of the digestive tract, a portion of a reproductive tract, either the female reproductive tract (e.g., a lumen of a fallopian tube) or the male reproductive tract (including various lumens including but not limited to the epididymis, vas deferens or ductul deferens, efferent duct, ampulla, seminal duct, ejaculatory duct, or urethra), the biliary tract, a nostril or nasal cavity, the oral cavity, the digestive tract, the tear ducts, or a glandular system. Other body lumens may be found in the auditory or visual system, or in interconnections thereof e.g., the Eustachian tubes. Some of the systems and devices described herein may be used in a body lumen through which fluid flows, but it is not intended that such devices or systems are limited to use in tubular lumen-containing structures containing moving fluid; in some applications an intraluminal device may be used in a body lumen containing relatively unmoving, or intermittently moving fluid.

The first intraluminal device 102 includes a body structure 106, a sensor 108, a processor 110, a data transmitter 112, and a wireless energy receiver 114. The first intraluminal device 102 is generally configured for diagnostic and treatment functionalities within the biological lumen, where the body structure 106 facilitates lumen travel by being dimensioned and structured to travel through the biological lumen. For example, the body structure 106 can adopt a capsule/structure or a pill shape/structure, or another shape or structure, to facilitate travel through the biological lumen. In an embodiment, the body structure 106 includes a hermetic seal to protect one or more components of the first intraluminal device 102 from the environment within the individual subject. In an embodiment, at least a portion of the first intraluminal device 102 comprises one or more of a biocompatible material, a biodegradable material, or a bioresorbable or bioabsorbable material (e.g., a natural or synthetic biodegradable or bioresorbable polymer, a bioresorbable ceramic or metal, silk, or paper). For example, at least a portion of the body structure 106 can include one or more of a biodegradable material or a bioresorbable material.

The sensor 108 is coupled to the body structure 106 and is oriented to detect at least one characteristic of the biological lumen and to generate one or more sense signals. In an embodiment, the sensor 108 generates the one or more sense signals upon detection of at least one characteristic of the biological lumen. In an embodiment, the sensor 108 constantly generates sense signals, even when no characteristics of the biological lumen are observed (e.g., null signals). The sensor 108 can include, but is not limited to, an optical device (e.g., an optical sensor such as a near infrared sensor or laser, or an imaging device such as a camera), a physiological sensor, a pH sensor, a pressure sensor, a temperature sensor, a chemical sensor, or a biosensor.

The processor 110 is operably coupled to the sensor 108 and is configured to receive the one or more sense signals from the sensor 108. The processor 110 includes components to process the one or more sense signals from the sensor 108 and to provide instruction to one or more components of the system 100, such as via one or more data signals. For example, the processor 110 can be configured to process the one or more sense signals to analyze whether the first intraluminal device 102 and the second intraluminal device 104 are properly positioned or in an appropriate condition for initializing or ceasing energy transfer. For example, the processor 110 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the processor 110 includes one or more ASICs having a plurality of predefined logic components. In one embodiment, the processor 110 includes one or more FPGAs having a plurality of programmable logic commands.

The data transmitter 112 is coupled to the body structure 106 and is configured to wirelessly transmit one or more data signals associated with the one or more sense signals from the sensor 108 responsive to instruction by the processor 110. For example, the data transmitter 112 can include one or more of an antenna structure, a transmitter structure, a transceiver structure, or the like, to wirelessly transmit data signals associated with observations made by the first intraluminal device 102 (e.g., via the sensor 108, a location determination device of system 100, or the like) or associated with instructions provided via the processor 110 for execution by other components of the system 100 (e.g., components of the first intraluminal device 102, components of the second intraluminal device 104, etc.), or to receive data signals, instructions, control commands, or the like from a device or system external to the system 100 or external to the intraluminal devices.

The wireless energy receiver 114 is coupled to the body structure 106 and is oriented to receive energy originating external to the first intraluminal device 102 to power at least one of the sensor 108, the processor 110, or the data transmitter 112. For example, the wireless energy receiver 114 can include one or more of an antenna structure, a receiver structure, or a transceiver structure, or the like, to wirelessly receive energy (e.g., one or more power signals) originating external to the first intraluminal device 102. In an embodiment, the wireless energy receiver 114 and the data transmitter 112 can include shared structural components to facilitate the operations of each of the wireless energy receiver 114 and the data transmitter 112 (e.g., the reception of power signals and the transmission of data signals). In an embodiment, the first intraluminal device 102 is operably coupled with the second intraluminal device 104 to facilitate transfer of energy from the second intraluminal device 104 to the wireless energy receiver 114 of the first intraluminal device 102 to provide power to one or more components of the first intraluminal device 102. In an embodiment, the first intraluminal device 102 includes a local energy storage component operably coupled with the wireless energy receiver 114 to store at least a portion of the energy received by the wireless energy receiver 114 for use by the first intraluminal device 102. For example, the local energy storage component can include, but is not limited to, a battery or a capacitive energy storage device.

The second intraluminal device 104 includes a second body structure 116 and an energy storage device 118. The second intraluminal device 104 is generally configured for supply or resupply power to the first intraluminal device 102, where the second body structure 116 facilitates lumen travel by being dimensioned and structured to travel through the biological lumen. For example, the second body structure 116 can adopt a capsule/structure or a pill shape/structure, or another shape or structure, to facilitate travel through the biological lumen to bring the second intraluminal device 104 within operating range of the first intraluminal device 102 to transfer energy from the second intraluminal device 104 to the first intraluminal device 102. In an embodiment, the body structure 116 includes a hermetic seal to protect one or more components of the second intraluminal device 104 from the environment within the individual subject. In an embodiment, at least a portion of the second intraluminal device 104 comprises one or more of a biocompatible material, a biodegradable material, or a bioresorbable or bioabsorbable material (e.g., a natural or synthetic biodegradable or bioresorbable polymer, a bioresorbable ceramic or metal, silk, or paper). For example, at least a portion of the body structure 116 can include one or more of a biodegradable material or a bioresorbable material.

Figure 2:
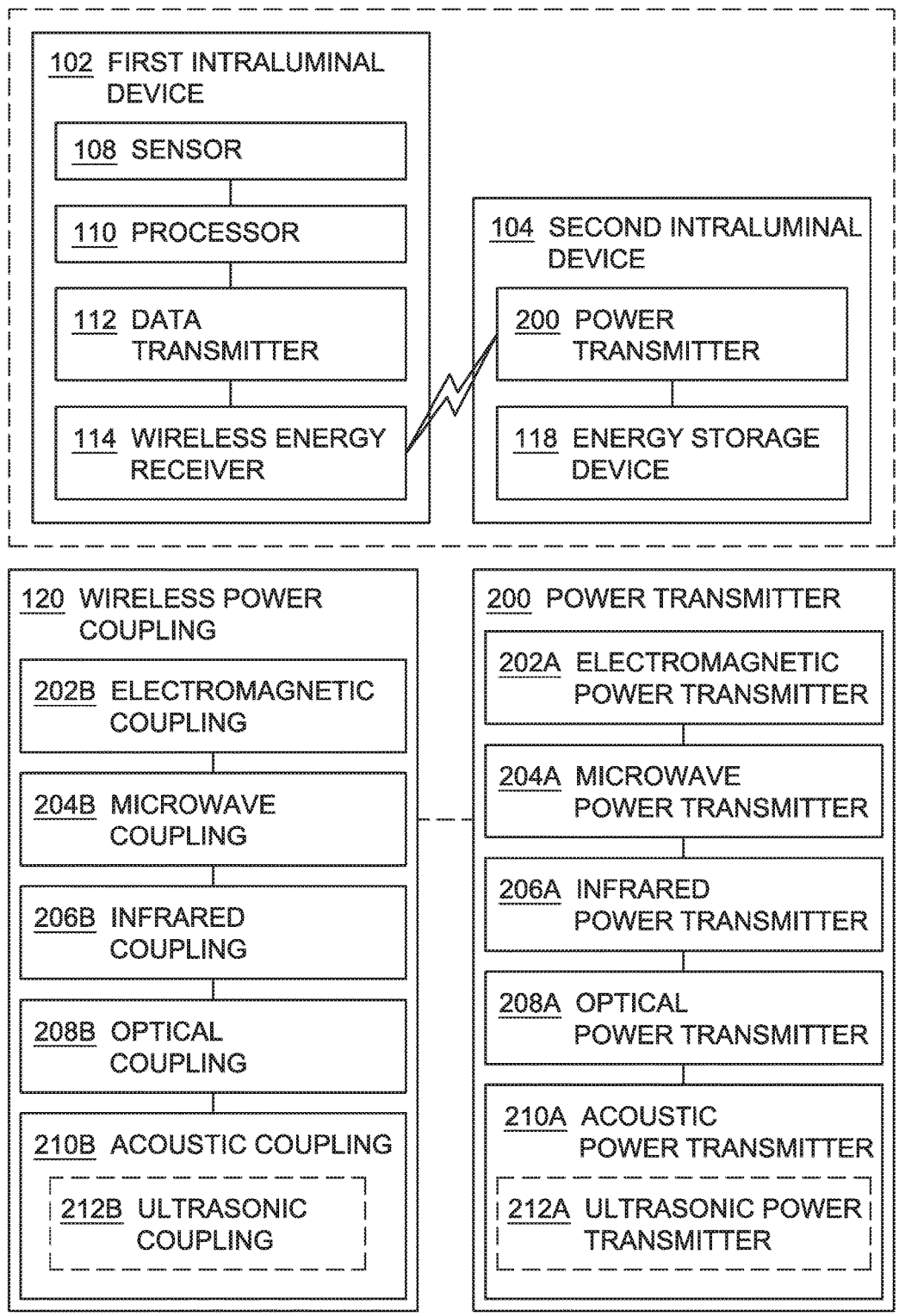
FIG. 2 is a schematic of an embodiment of a system such as shown in FIG. 1.

The energy storage device 118 is coupled to the second body structure 116 and is configured to wirelessly transfer energy stored in the energy storage device 118 to the wireless energy receiver 114 of the first intraluminal device 102 when the first intraluminal device 102 and the second intraluminal device 104 are positioned within the subject (e.g., FIG. 1 displays the first intraluminal device 102 and the second intraluminal device 104 positioned within the gastrointestinal system of the subject). The wireless transfer of energy from the energy storage device 118 to the wireless energy receiver 114 can occur over a wireless power coupling 120. In an embodiment, shown in FIG. 2, the second intraluminal device 104 includes a power transmitter 200 coupled to the energy storage device 118, where the power transmitter 200 transfers energy stored in the energy storage device 118 via the wireless power coupling 120 to the wireless energy receiver 114 of the first intraluminal device 102. In an embodiment, the power transmitter 200 includes an electromagnetic power transmitter 202a having an electromagnetic coupling 202b between the energy storage device 118 and the wireless energy receiver 114. In an embodiment, the power transmitter 200 includes a microwave power transmitter 204a having a microwave coupling 204b between the energy storage device 118 and the wireless energy receiver 114. In an embodiment, the power transmitter 200 includes an infrared power transmitter 206a having an infrared coupling 206b between the energy storage device 118 and the wireless energy receiver 114. In an embodiment, the power transmitter 200 includes an optical power transmitter 208a having an optical coupling 208b between the energy storage device 118 and the wireless energy receiver 114. In an embodiment, the power transmitter 200 includes an acoustic power transmitter 210a having an acoustic coupling 210b between the energy storage device 118 and the wireless energy receiver 114. For example, the acoustic power transmitter 210a can include, but is not limited to, an ultrasonic power transmitter 212a having an ultrasonic coupling 212b between the energy storage device 118 and the wireless energy receiver 114. In an embodiment, the power transmitter 200 is integrated in the energy storage device 118. The amount of power transmitted from the second intraluminal device 104 to the first intraluminal power device 102 can be sufficient to power components of the first intraluminal device (e.g., multi-functional feature components, high resolution video components, surgical components, lasing components, motive components, or the like), and can be, for example, from about 200 mW to about 1000 mW. In an embodiment, the amount of power transferred can exceed 1000 mW.

The transfer of energy between the energy storage device 118 and the wireless energy receiver 114 can be initiated according to one or more activation protocols, which can depend on factors including, but not limited to, identification of one or more of the first intraluminal device 102 or the second intraluminal device 104, identification of one or more environmental conditions within the individual subject, identification of an absolute or relative position of one or more of the first intraluminal device 102 or the second intraluminal device 104, identification of an energy transfer efficiency between the first intraluminal device 102 and the second intraluminal device 104, external control instructions, or through other activation protocols.

Figure 3A:
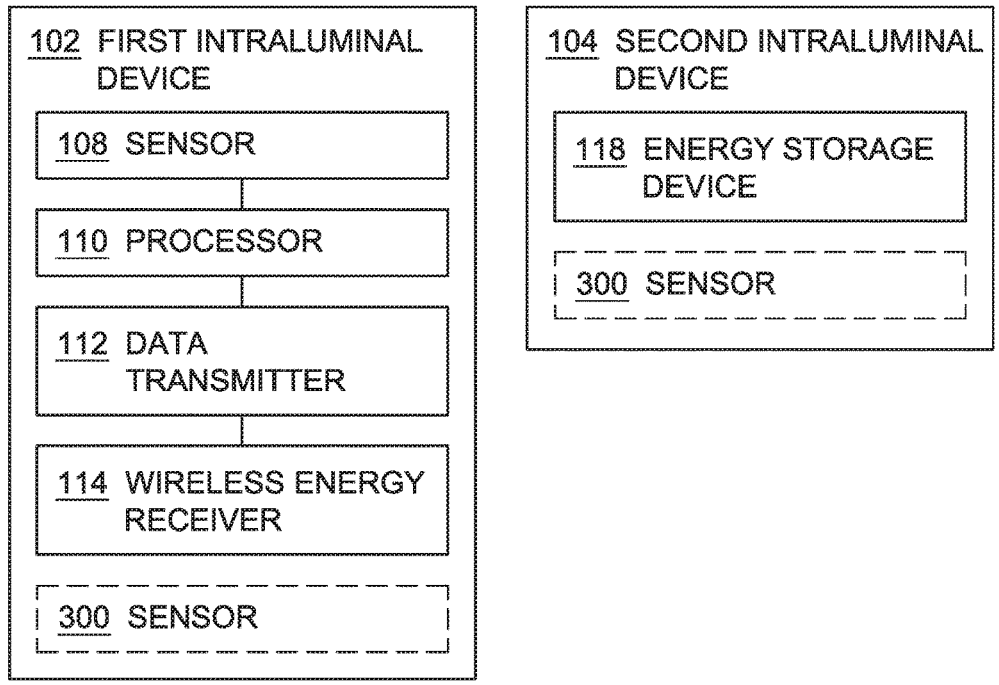
FIG. 3A is a schematic of an embodiment of a system such as shown in FIG. 1.
Figure 3B:
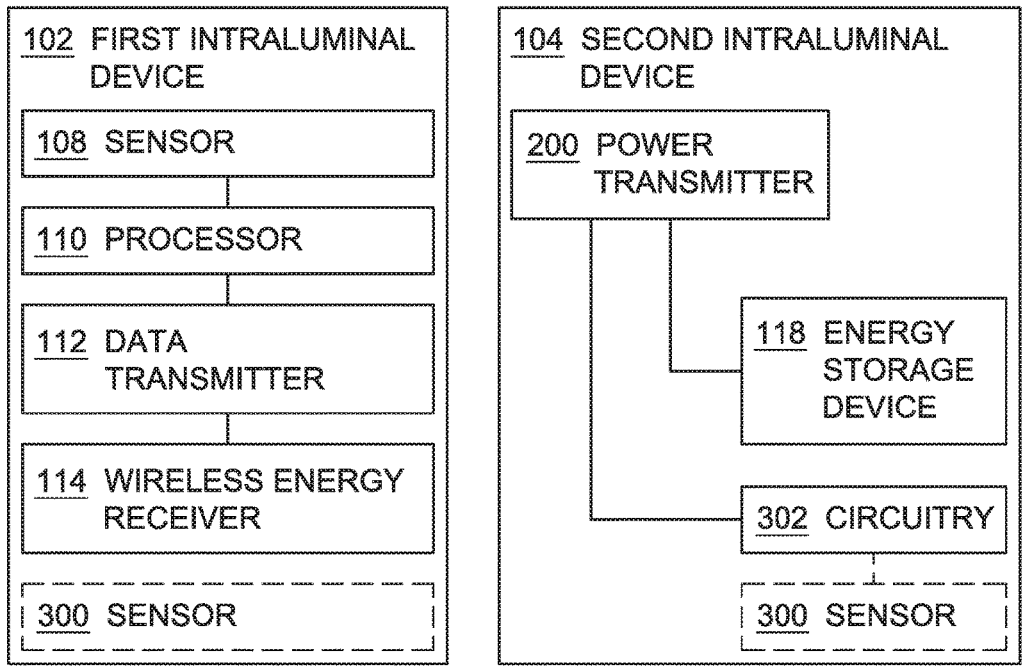
FIG. 3B is a schematic of an embodiment of a system such as shown in FIG. 1.
Figure 3C:
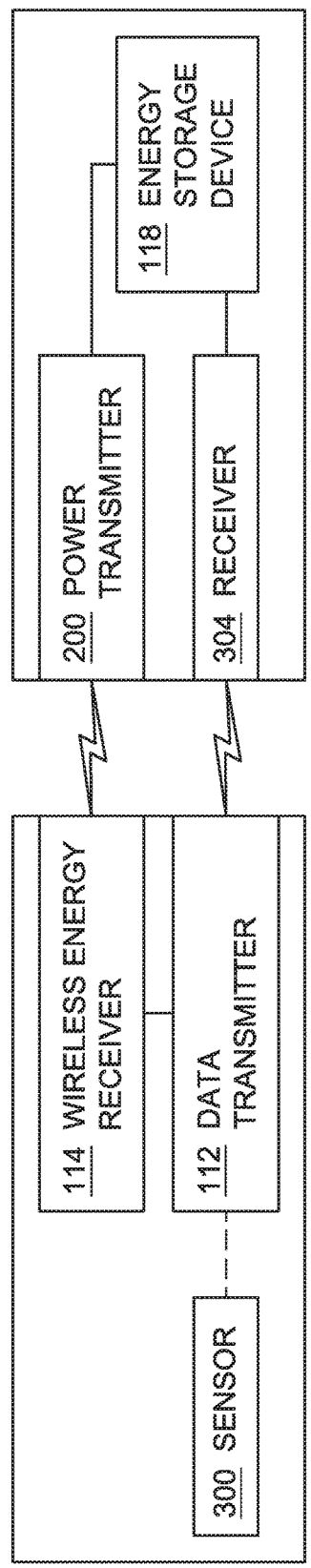
FIG. 3C is a schematic of an embodiment of a system such as shown in FIG. 1.

For example, in an embodiment, shown in FIGS. 3A-3C, at least one of the first intraluminal device 102 or the second intraluminal device 104 includes at least one sensor 300 configured to detect the other of the first intraluminal device 102 or the second intraluminal device 104. The sensor 300 can be operable to detect one or more of the first intraluminal device 102 or the second intraluminal device 104 to identify one or more characteristics of the respective devices, including but not limited to, a location of one of the respective devices relative to the other of the respective devices, a distance between the respective devices, an orientation of one of the respective devices relative to the other of the respective devices, or an angular orientation of one of the respective devices relative to the other of the respective devices. Additionally or alternatively, in an embodiment, the sensor 300 can be or can utilize a location-determination device of the system 100 configured to determine the relative or absolute positions of the first intraluminal device 102 or the second intraluminal device 104 (further described below). In an embodiment, the second intraluminal device 104 includes circuitry 302 that causes the power transmitter 200 to transfer energy (e.g., via power coupling 120) stored in the energy storage device 118 to the wireless energy receiver 114 of the first intraluminal device 102 responsive to reaching a threshold distance between the first intraluminal device 102 and the second intraluminal device 104. For example, the sensor 300 can detect a distance between the first intraluminal device 102 and the second intraluminal device 104 and generate one or more sense signals responsive thereto, whereby the circuitry 302 can receive the one or more sense signals to initiate power transfer when the one or more sense signals are indicative of reaching or being within a threshold distance between the first intraluminal device 102 and the second intraluminal device 104. Alternatively or additionally, the first intraluminal device 102 can communicate (e.g., via data transmitter 112) instructions to the second intraluminal device 104 (which can be received via a receiver 304 (e.g., antenna, transceiver, etc.)) to initiate power transfer when the one or more sense signals are indicative of reaching or being within a threshold distance between the first intraluminal device 102 and the second intraluminal device 104, such as when the sensor 300 is positioned on the first intraluminal device 102 (shown in FIG. 3C). In an embodiment, the receiver 304 is incorporated in the power transmitter 200, such as via a transceiver structure. The determination of whether the distance between the first intraluminal device 102 and the second intraluminal device 104 is at or within a threshold distance can be performed by one or more of the processor 110 or the circuitry 302, where the threshold distance can be a stored value that can depend on power transfer considerations (e.g., constraints of the power transmitter 200, of the power coupling 120, etc.), can depend on particular environmental considerations (e.g., biological characteristics associated with the biological lumen, surrounding tissue or bodily fluids, etc., which can influence power transfer), or the like.

In an embodiment, the circuitry 302 causes the power transmitter 200 to transfer energy (e.g., via power coupling 120) stored in the energy storage device 118 to the wireless energy receiver 114 of the first intraluminal device 102 responsive to an orientation of the first intraluminal device 102 relative to the second intraluminal device 104. For example, the sensor 300 can detect an orientation of the first intraluminal device 102 relative to the second intraluminal device 104 and generate one or more sense signals responsive thereto, whereby the circuitry 302 can receive the one or more sense signals to initiate power transfer when the one or more sense signals are indicative of a particular orientation of the first intraluminal device 102 relative to the second intraluminal device 104 suitable for power transfer. Alternatively or additionally, the first intraluminal device 102 can communicate (e.g., via data transmitter 112) instructions to the second intraluminal device 104 (which can be received via the receiver 304) to initiate power transfer when the one or more sense signals are indicative of a particular orientation of the first intraluminal device 102 relative to the second intraluminal device 104 suitable for power transfer. The determination of whether the orientation of the first intraluminal device 102 relative to the second intraluminal device 104 is suitable for power transfer can be performed by one or more of the processor 110 or the circuitry 302. For example, one or more of the processor 110 or the circuitry 302 can include or can access an orientation-determination module to provide one or more algorithms to determine whether the measured orientation between the first intraluminal device 102 relative to the second intraluminal device 104 would be suitable for power transfer or would fall within a predetermined range of orientations suitable for power transfer. The orientations suitable for power transfer can depend on power transfer considerations (e.g., constraints of the power transmitter 200, of the power coupling 120, etc.), can depend on particular environmental considerations (e.g., biological characteristics associated with the biological lumen, surrounding tissue or bodily fluids, etc., which can influence power transfer), or the like. In an embodiment, the circuitry 302 causes the power transmitter 200 to transfer energy stored in the energy storage device 118 to the wireless energy receiver 114 of the first intraluminal device 102 responsive to an angular orientation of the first intraluminal device 102 relative to the second intraluminal device 104.

In an embodiment, the power transmitter 200 transfers energy (e.g., via power coupling 120) stored in the energy storage device 118 to the wireless energy receiver 114 of the first intraluminal device 102 responsive to an energy transfer efficiency between the energy storage device 118 and the wireless energy receiver 114 being above a threshold efficiency. For example, one or more of the processor 110 or the circuitry 302 can make a determination of energy transfer efficiency (e.g., based on sense signals generated by the sensor 300), which can depend on a distance between the first intraluminal device 102 and the second intraluminal device 104, an orientation of the first intraluminal device 102 relative to the second intraluminal device 104, a density or composition of biological material separating the first intraluminal device 102 and the second intraluminal device 104, or the like. For example, one or more of the processor 110 or the circuitry 302 can include or can access an energy transfer efficiency determination module to provide one or more algorithms to determine whether the positioning of the first intraluminal device 102 relative to the second intraluminal device 104 would be suitable for power transfer (e.g., would meet a predetermined energy transfer efficiency).

Figure 3D:
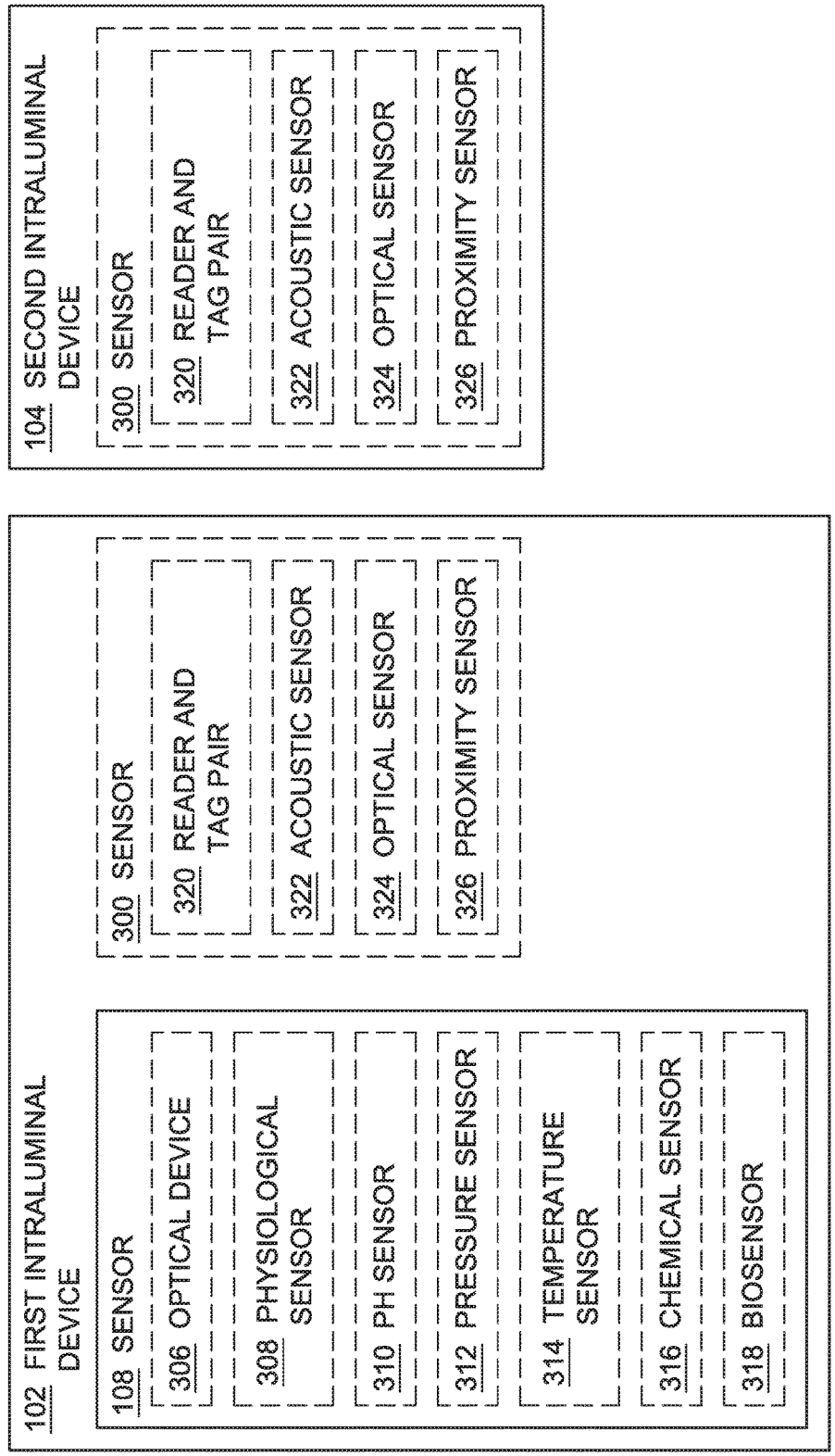
FIG. 3D is a schematic of an embodiment of a system such as shown in FIG. 1.

In an embodiment, shown in FIG. 3D, the sensor 108 can include, but is not limited to, an optical device 306 (e.g., an optical sensor, a camera, etc.), a physiological sensor 308 (e.g., a pH sensor, temperature sensor, oximeter, pressure sensor, electrical conductivity sensor, etc.), a pH sensor 310 (e.g., to detect a pH indicating position within a gastrointestinal tract), a pressure sensor 312, a temperature sensor 314 (e.g., to detect whether the device is in the body or has been eliminated), a chemical sensor 316, or a biosensor 318. A physiological sensor can include a sensor able to measure a physiological parameter; for example, physiological parameters in the gastrointestinal tract that are routinely of interest to physicians include temperature, pH, pressure, oxygenation, and electrical conductivity, while a physiological parameter of the viscosity of mucus (e.g., identified by imaging) would be of interest in a respiratory tract of a cystic fibrosis patient.

Physiological sensors can include chemical sensors and biosensors. For example, without limitation, a chemical sensor can detect a chemical signature of an analyte, for example an analyte of a physiological origin (e.g., a cellular mmcompound, a secreted compound such as an antibody or a cytokine, or a metabolite) or an analyte of an exogenous origin (e.g., an ingested or inhaled substance, such as a drug, or a tagging or labeling compound such as might be released from the first intraluminal device 102 or provided separately). Examples of chemical sensors include, but are not limited to, sensors having recognition elements, electronic chip sensors, microbalance sensors, and near infrared spectrometers. A biosensor can detect a biochemical or biological element. Biosensors include, for example but are not limited to, sensors having a biological recognition element able to bind an analyte of interest (e.g., an aptamer-based microcantilever) and sensors utilizing an enzyme with recognition and reaction properties. In an embodiment, chemical sensors or biosensors can include molecular sensor or nanosensor aspects.

In an embodiment, shown in FIG. 3D, the sensor 300 can include, but is not limited to, a reader and tag pair 320, an acoustic sensor 322, an optical sensor 324, or a proximity sensor 326. For example, the reader and tag pair 320 can include an RFID tag and reader pair, where one of the first intraluminal device 102 or the second intraluminal device 104 can include the RFID tag, and the other of the first intraluminal device 102 or the second intraluminal device 104 can include the reader configured to detect a presence and/or identify the other of the first intraluminal device 102 or the second intraluminal device 104 based on recognition of the RFID tag. The acoustic sensor 322 can detect and/or identify the first intraluminal device 102 (e.g., when the acoustic sensor 322 is located on the second intraluminal device 104) or the second intraluminal device 104 (e.g., when the acoustic sensor 322 is located on the first intraluminal device 102) based on detected acoustic signals. For example, the acoustic sensor 322 can be configured to emit an acoustic signal (e.g., ultrasonic signal, radio-frequency signal, etc.) and detect a reflected signal, such as a reflected acoustic signal that is reflected by the first intraluminal device 102 or the second intraluminal device 104. For example, the acoustic sensor 322 on the first intraluminal device 102 or the second intraluminal device 104 can be configured to detect an acoustic signal emitted by the other of the first intraluminal device 102 or the second intraluminal device 104. The optical sensor 324 can detect and/or identify the first intraluminal device 102 (e.g., when the optical sensor 324 is located on the second intraluminal device 104) or the second intraluminal device 104 (e.g., when the optical sensor 324 is located on the first intraluminal device 102) based on detected optical signals. For example, the optical sensor 324 can include, but is not limited to, an imaging device (e.g., a camera to generate a visual image of an intraluminal device or environment), a photodetector (e.g., e.g., to detect one or more electromagnetic signals reflected from a surface of an intraluminal device or environmental feature), or the like. The proximity sensor 326 can detect and/or identify the first intraluminal device 102 (e.g., when the proximity sensor 326 is located on the second intraluminal device 104) or the second intraluminal device 104 (e.g., when the proximity sensor 326 is located on the first intraluminal device 102) based on detected proximity between the respective intraluminal devices. For example, the proximity sensor 326 can include, but is not limited to, a pressure sensor (e.g., to detect pressure differentials associated with the presence of an object within an environment), an electromagnetic proximity sensor (e.g., to detect and/or identify an intraluminal device or environmental feature based on detected electromagnetic signals, such as a bolometer or thermal imaging device), or the like.

Figure 4:
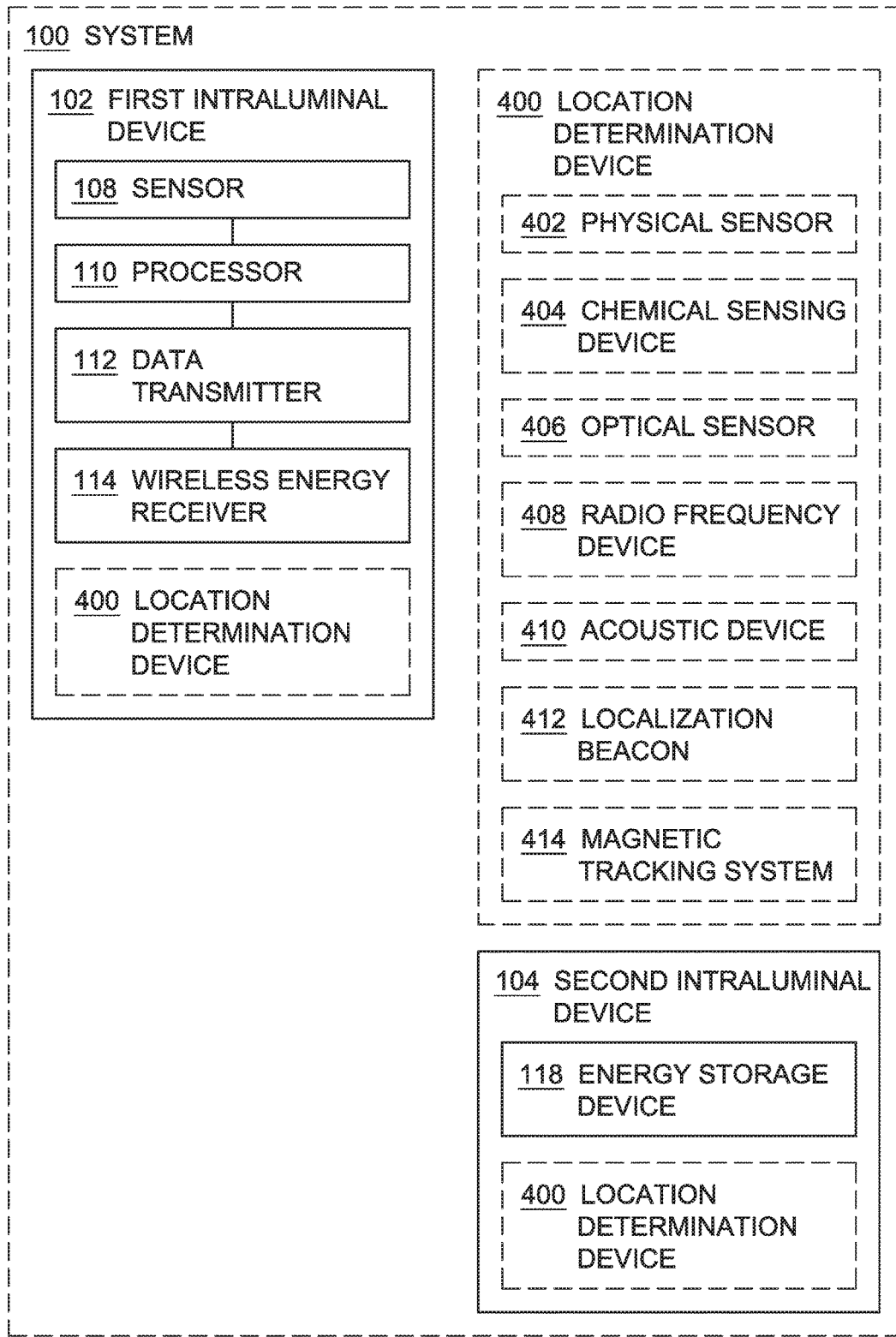
FIG. 4 is a schematic of an embodiment of a system such as shown in FIG. 1.

In an embodiment, shown in FIG. 4, the system 100 includes a location determination device 400 configured to determine at least one of an absolute location or a relative location of at least one of the first intraluminal device 102 or the second intraluminal device 104. In an embodiment, the location determination device 400 can be operable to determine an absolute location of one of the first intraluminal device 102 or the second intraluminal device 104 within the lumen, including its position in three-dimensional (3D) space, the distance it has travelled along the lumen, and the region of the lumen in which it is located. In an embodiment, the location determination device 400 can be operable to determine a location of the first intraluminal device 102 or the second intraluminal device 104 and can inform the processor 110 of the first intraluminal device 102 or the second intraluminal device 104 in regards to its motion. For example, the location determination device 400 can be operable to determine a location of the first intraluminal device 102 within a gastrointestinal tract and, if the location meets a pre-defined location (e.g., the small intestine or a site where the device must remain for some time), can inform the processor 110 to direct a motive structure of the first intraluminal device 102 or the second intraluminal device (e.g., motive structure 700 described further herein) to move in a particular direction or direct a motion-resistive mechanism of the first intraluminal device 102 or the second intraluminal device (e.g., motion-resistive mechanism 900 described further herein) to halt motion (e.g., by engaging the wall of the lumen). For example, the location determination device 400 can be operable to determine a relative location of the second intraluminal device 104 relative to the first intraluminal device 102 and inform the processor 110, which can direct the motive structure to induce movement toward the first intraluminal device 102. In an embodiment, the location determination device 400 can be operable to determine a relative location of one of the first intraluminal device 102 or the second intraluminal device 104 relative to the other of the first intraluminal device 102 or the second intraluminal device 104, such as to determine when to initiate power transfer from the second intraluminal device 104 to the first intraluminal device 102. The location determination device 400 can include, but is not limited to, one or more of a physical sensor 402 (e.g., time sensor, distance sensor, flow sensor, or pressure sensor), a chemical sensing device 404 (e.g., a pH sensor or chemical sensor, which may be or utilize sensor 108), an optical sensor 406 (e.g., a laser, near infrared sensor, or imaging sensor), a radio frequency device 408 (e.g., for triangulation), an acoustic device 410 (e.g., acoustic source localization device or ultrasound), a localization beacon 412, or a magnetic tracking system 414. In an embodiment, the location determination device can include an external component external to the intraluminal devices. In an embodiment, the processor 110 is configured to control an angular sensitivity of at least one of the wireless energy receiver 114 or the energy storage device 118 based on the at least one of the absolute location or the relative location determined via the location determination device 400. The angular sensitivity can be controlled via motion of the first intraluminal device 102 or the second intraluminal device (described further herein), via motion of one or more individual components of the first intraluminal device 102 or the second intraluminal device (e.g., the wireless energy receiver 114, the energy storage device 118, etc.). For example, the processor 110 can receive one or more signals (e.g., location signals) from the location determination device 400 and make a determination about whether an angular sensitivity of at least one of the wireless energy receiver 114 or the energy storage device 118 should be adjusted, which can depend on the power transfer considerations, a power level of at least one of the first intraluminal device 102 or the second intraluminal device 104, or the like.

Figure 5:
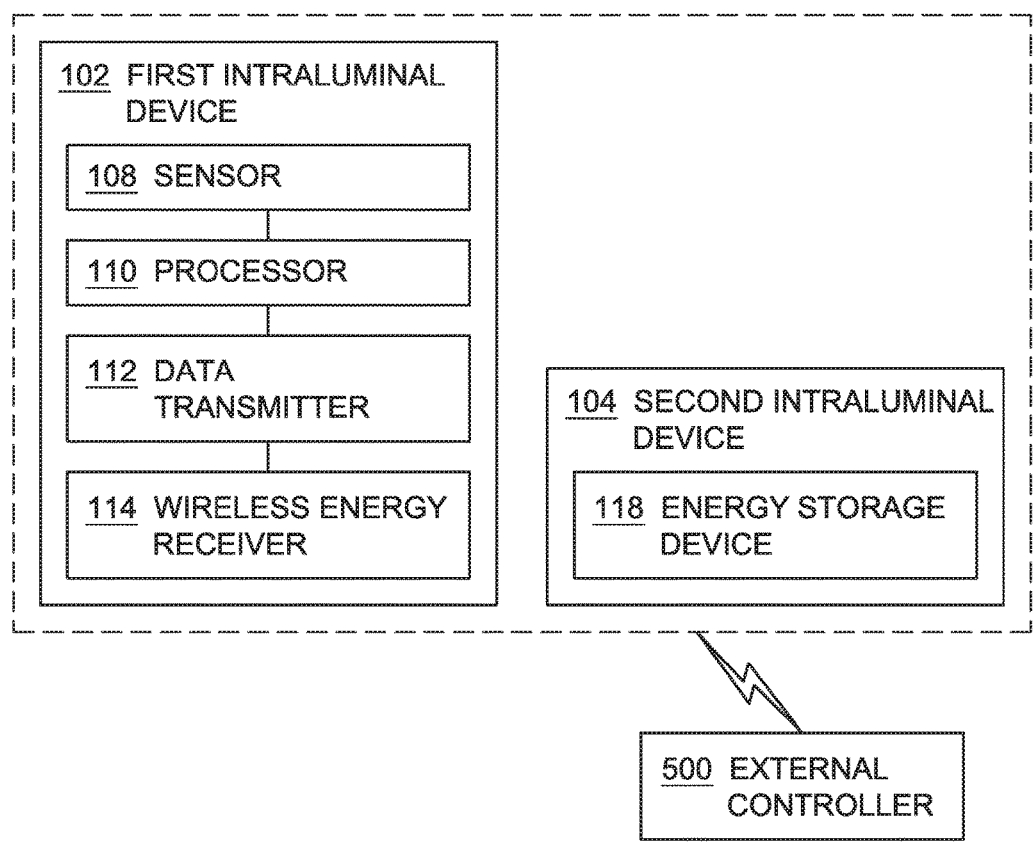
FIG. 5 is a schematic of an embodiment of a system such as shown in FIG. 1.

In an embodiment, shown in FIG. 5, at least one of the first intraluminal device 102 or the second intraluminal device 104 is controllable via an external controller 500. For example, the external controller 500 can be positioned external to the body of the individual subject to provide control signals to one or more components of the system 100. In an embodiment, the external controller 500 is operable to send one or more control signals to a receiver of one or more of the first intraluminal device 102 (e.g., the wireless energy receiver 114, another receiving device, etc.) or the second intraluminal device 104 (e.g., receiver 304, a component of power transmitter 200, etc.). One or more of the processor 110 or the circuitry 302 can receive the control signals from the external controller 500 for execution of the commands, including, but not limited to, initiation of transfer of energy, ceasing of transfer of energy, repositioning of one or more of the first intraluminal device 102 or the second intraluminal device, activation or deactivation of one or more components of one or more of the first intraluminal device 102 or the second intraluminal device (e.g., sensor 108, data transmitter 112, sensor 300, etc.), or the like. In an embodiment, the external controller 500 includes a communication device, such as one or more of a mobile communication device or a computer system including, but not limited to, mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The external controller 500 can communicate (e.g., send and receive communication signals) with one or more components of system 100 via one or more connected or wireless communication mechanisms including, but not limited to acoustic communication signals, optical communication signals, radio communication signals, infrared communication signals, ultrasonic communication signals, or the like.

Figure 6A:
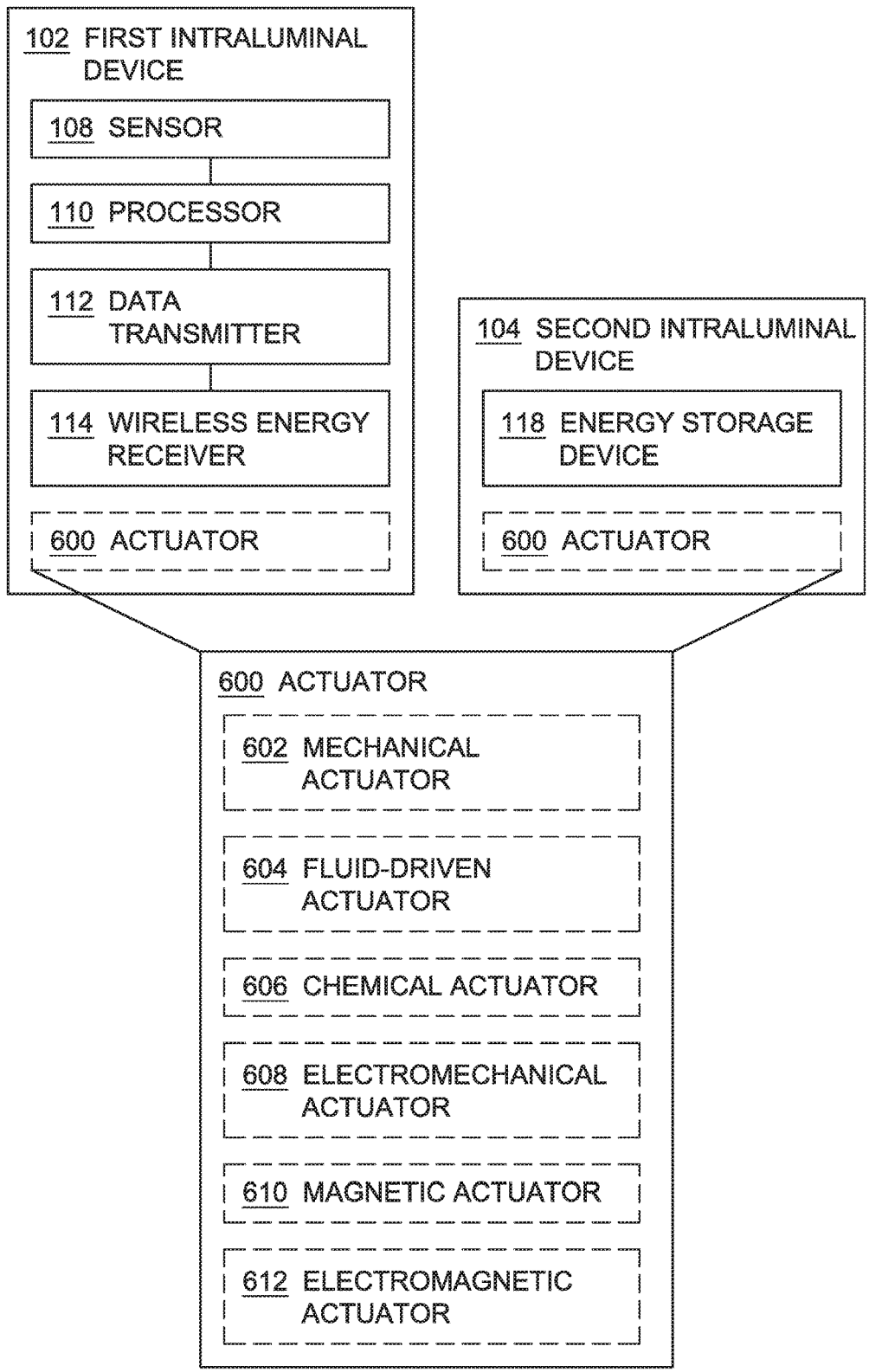
FIG. 6A is a schematic of an embodiment of a system such as shown in FIG. 1.
Figure 6B:
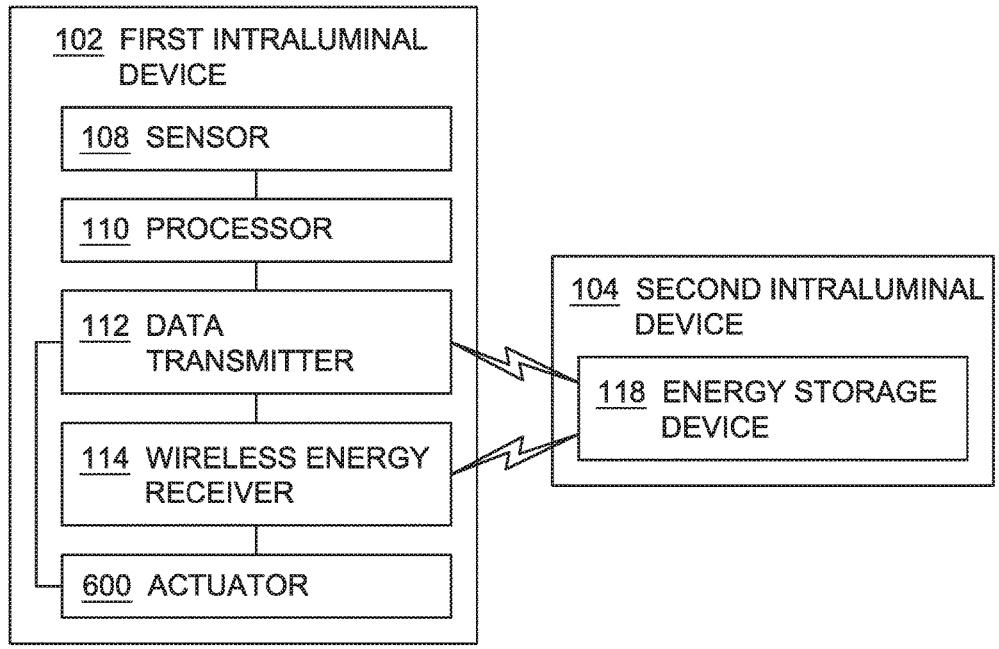
FIG. 6B is a schematic of an embodiment of a system such as shown in FIG. 1.
Figure 6C:
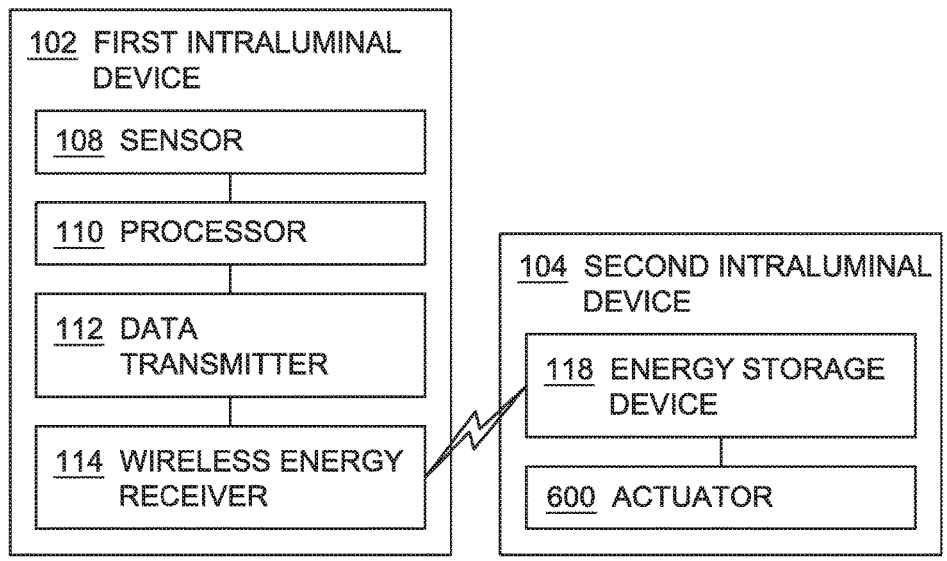
FIG. 6C is a schematic of an embodiment of a system such as shown in FIG. 1.

In an embodiment, shown in FIGS. 6A-6E, at least one of the first intraluminal device 102 or the second intraluminal device 104 includes an actuator 600 configured to initiate transfer of energy from the energy storage device 118 to the wireless energy receiver 114. The actuator 600 can include, but is not limited to, a mechanical actuator 602, a fluid-driven actuator 604, a chemical actuator 606, an electromechanical actuator 608, a magnetic actuator 610, or an electromagnetic actuator 612. For example, the actuator 600 can initiate transfer of energy based on conditions surrounding one or more of the first intraluminal device 102 or the second intraluminal device, by a position of one or more of the first intraluminal device 102 or the second intraluminal device, by external command, or the like, which can be facilitated by the location determination device 400, one or more sensors of the system 100 (e.g., sensor 108, sensor 300), one or more receivers of the system 100 (e.g., receiver 304, wireless energy receiver 114, etc.), or by another component of the system 100. For example, transfer can be initiated upon reaching a certain position within the individual's body determined by fluid flow or pressure measurements or by the location determination device 400 (e.g., for operation of the first intraluminal device 102 within the respiratory system), determined by pH (e.g., for operation of the first intraluminal device 102 within a particular portion of the gastrointestinal system having a particular pH); transfer is initiated upon reaching a portion of the body having particular electromagnetic characteristics (e.g., for operation of the first intraluminal device within a particular portion of the nervous system), or the like). Referring to FIG. 6B, the first intraluminal device 102 can include the actuator 600, whereby the actuator 600 can initiate transfer of energy from the energy storage module 118 of the second intraluminal device 104, such as through communication signals transmitted from the data transmitter 112 or other communications component. Referring to FIG. 6C, the second intraluminal device 104 can include the actuator 600 where the actuator 600 can initiate transfer of energy from the energy storage module to the wireless energy receiver 114 of the first intraluminal device 102.

Figure 6D:
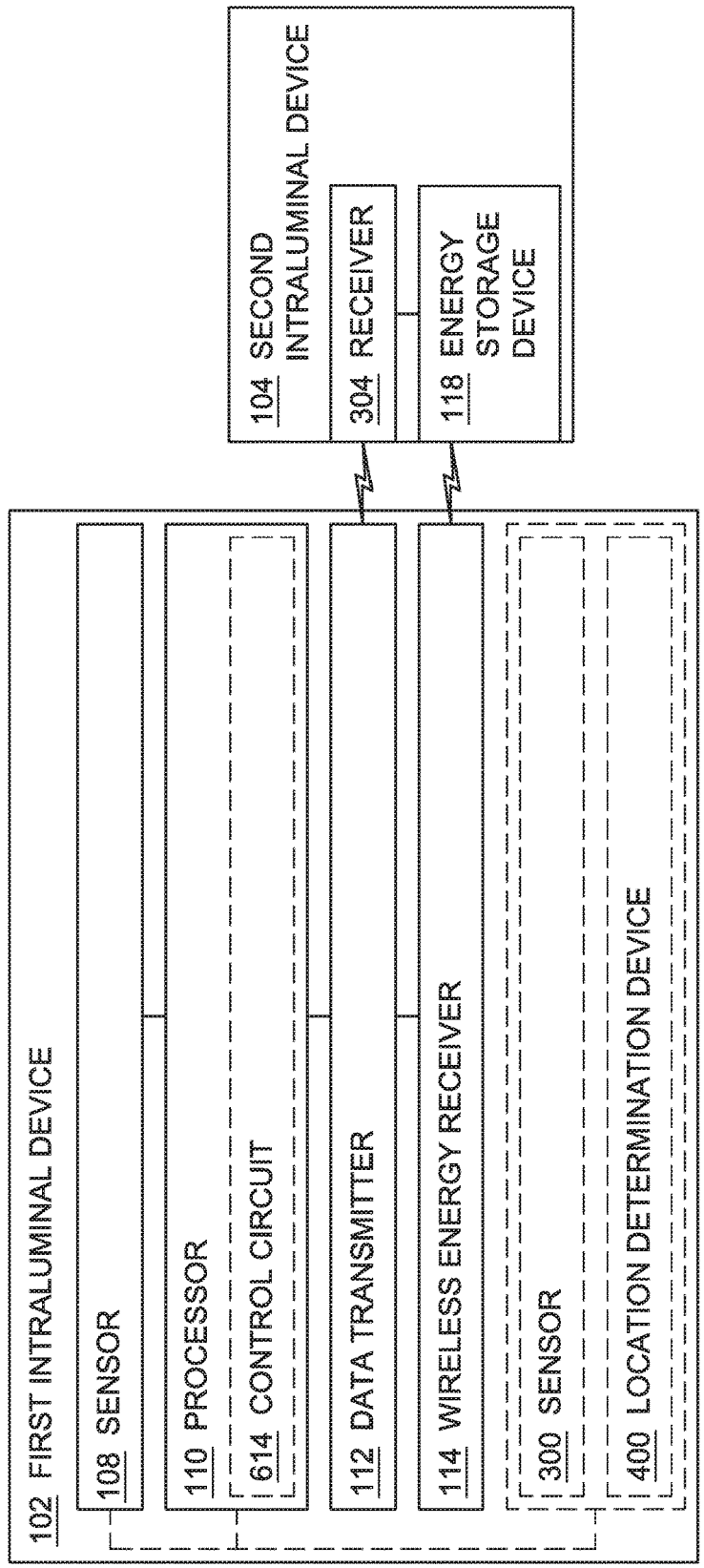
FIG. 6D is a schematic of an embodiment of a system such as shown in FIG. 1.

Referring to FIG. 6D, the processor 110 of first intraluminal device 102 can include (or can be operably coupled to) a control circuit 614, where the control circuit 614 can drive actuation of the actuator 600 in response to one or more of a timer output, a sensor output, or a communication received from a source external to the individual subject (e.g., from the external controller 500). For example, the control circuit 614 can be coupled to one or more of the location determination device 400, the sensor 108, the sensor 300, or other component that can generate one or more signals to identify a time or condition under which actuation of the actuator 600 should occur. For example, the actuator 600 can initiate transfer of energy based on a time period since introduction of the first intraluminal device 102 or the second intraluminal device 104 to the biological lumen, based on external control by a medical professional or other user, or based on conditions surrounding one or more of the first intraluminal device 102 or the second intraluminal device (e.g., transfer is initiated upon reaching a certain position within the individual's body determined by fluid flow or pressure (e.g., for operation of the first intraluminal device 102 within the respiratory system), determined by pH (e.g., for operation of the first intraluminal device 102 within a particular portion of the gastrointestinal system having a particular pH); transfer is initiated upon reaching a portion of the body having particular electromagnetic characteristics (e.g., for operation of the first intraluminal device within a particular portion of the nervous system), or the like). Referring to FIG. 6E, the second intraluminal device 104 can include the control circuit 614, which can be coupled to one or more of the location determination device 400, the sensor 300, the sensor 108 (e.g., via a communication link between the first intraluminal device 102 and the second intraluminal device 104, such as between the data transmitter 112 and the receiver 304), or other component that can generate one or more signals to identify a time or condition under which actuation of the actuator 600 should occur.

Figure 7:
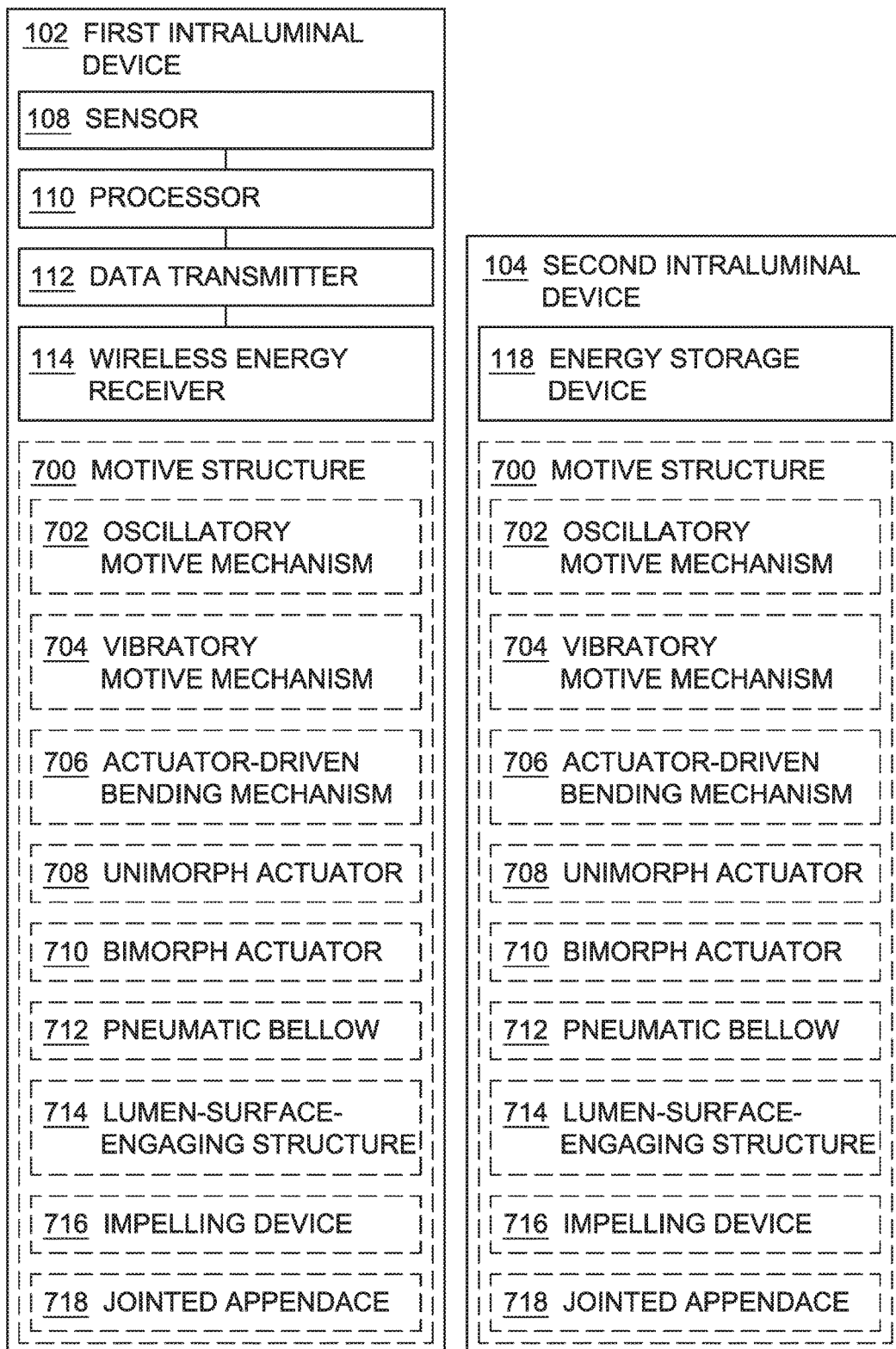
FIG. 7 is a schematic of an embodiment of a system such as shown in FIG. 1.

In an embodiment, shown in FIG. 7, at least one of the first intraluminal device 102 or the second intraluminal device 104 includes a motive structure 700 operable to provide movement (e.g., alteration of position, orientation, etc.) to the respective intraluminal devices. As described herein, the positioning and/or orientation of the intraluminal devices can influence power transfer conditions, such as triggers for initiation of power transfer, efficiency of power transfer, or the like. The motive structure 700 can include, but is not limited to, one or more of an oscillatory motive mechanism 702, a vibratory motive mechanism 704, an actuator-driven bending mechanism 706, a unimorph actuator 708, a bimorph actuator 710, a pneumatic bellow 712, a lumen-surface-engaging structure 714, an impelling device 716, or a jointed appendage 718. For example, in an embodiment, an intraluminal device includes at least one inchworm-like motive mechanism, in which at least a portion of an intraluminal device intermittently engages and disengages from the surface thereby traversing a distance. For example, an intraluminal device can include an inchworm motor. For example, an intraluminal device can include an inchworm actuator. For example, an intraluminal device can include a stick and slip mechanism. In an embodiment, an intraluminal device includes at least one earthworm-like motive mechanism, in which at least a portion of an intraluminal device is adjacently displaced along the surface thereby traversing a distance. In an embodiment an intraluminal device includes mechanism inducing forced bending vibrations of continua of an intraluminal device driven by actuators such as piezoelectric bending actuators. The locomotion direction of an intraluminal device can be controlled by the excitation frequencies of the actuation element. In an embodiment, an intraluminal device may include a piezoelectric unimorph actuator or a piezoelectric bimorph actuator. In an embodiment, an intraluminal device can include at least one actuator that drives the movement of at least a portion of an intraluminal device and the engagement of the surface. For example, an intraluminal device might include two-way linear actuators using springs made from a shape memory alloy. For example, an intraluminal device might include a piezoelectric microactuator. For example, an intraluminal device might include a micromotor. In an embodiment an intraluminal device is jointed between sections of an intraluminal device, and one or more actuators drive each section, for example in an inchworm- or earthworm-like fashion. In an embodiment, an intraluminal device includes an expandable bellow, for example, a pneumatic bellows, that provides the locomotive mechanism. In an embodiment, an intraluminal device includes surface-engaging protrusions, microprotrusions, setae, micropilli, or adhesive micropilli. In an embodiment, at least a portion of an intraluminal device includes micro-patterning on the surface, e.g., for friction enhancement. In an embodiment, an intraluminal device includes at least one motive mechanism configured to touch, grasp, grip, or otherwise engage the surface tissue of the lumen.

In an embodiment, the impelling device 716 is configured to engage the lumen tissue and provide locomotion to an intraluminal device; for example, an impelling device might comprise one or more appendages, legs, or wheels, with or without adhesive aspects, e.g., adhesive micropilli. One or more actuators or motors can be used to drive impelling devices. Examples of actuators include piezoelectric, DC motors, electromagnetic, and electrostatic actuators. In addition, actuators can be formed from shape memory alloys or ionic polymer metal components. In an embodiment an intraluminal device includes jointed appendages and legs that can be actuated to propel an intraluminal device forward in a walking or crawling motion. For example, a legged locomotion system can include a slot-follower mechanism driven via lead screw to provide propulsive force to a jointed leg. For example, multiple jointed legs, e.g., of superelastic or other material, can be motivated to interact with the surface under control of a motor, e.g., a brushless minimotor. For example, appendages or legs can be formed from shape memory alloy and driven by the application of current. For example, appendages can act to engage the surface driven by rotational forces to provide locomotion. For example, wheels can be driven by motors or other actuators. In an embodiment, actuators include microelectromechanical systems.

Figure 8:
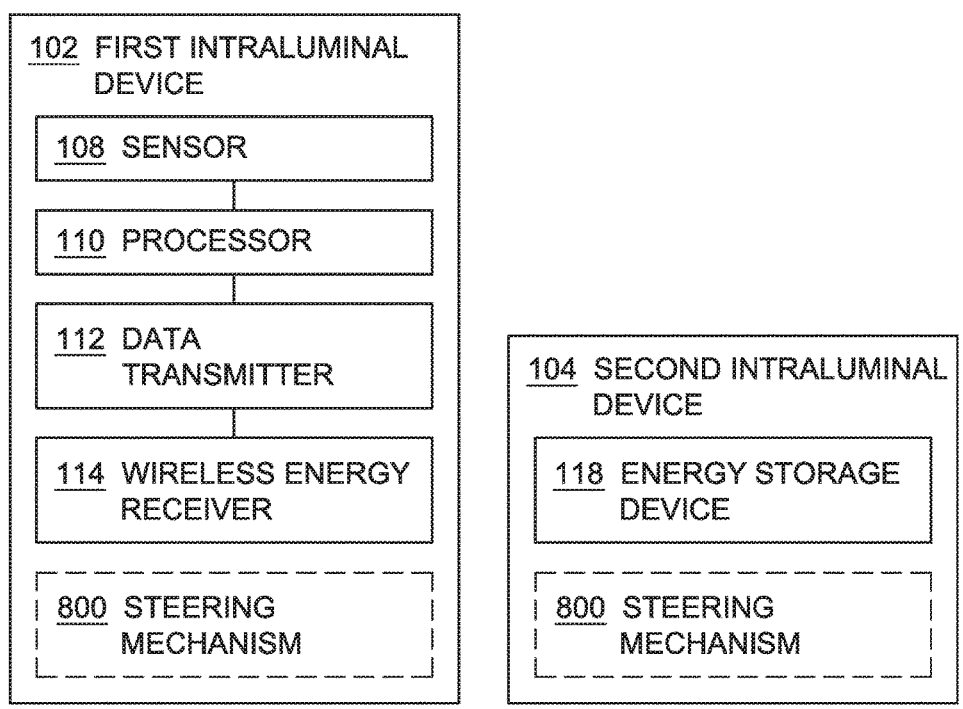
FIG. 8 is a schematic of an embodiment of a system such as shown in FIG. 1.

In an embodiment, shown in FIG. 8, at least one of the first intraluminal device 102 or the second intraluminal device 104 includes a steering mechanism 800. For example, the steering mechanism 800 can be operable to alter a direction of travel of first intraluminal device 102 or the second intraluminal device 104. The steering mechanism 800 can be utilized as an alternative to the motive structure 700 or in addition to the motive structure 700 (e.g., to provide directional change during motion). For example, in an embodiment, an intraluminal device is configured to employ one or more impelling mechanisms in a manner to provide movement in a particular direction. For example, to change direction (e.g., as directed by a controller), only a portion of multiple appendages (or legs or wheels) can be actuated, thereby moving a portion of an intraluminal device so that the intraluminal device heads in a new direction and allowing an intraluminal device to be steered. In an embodiment an intraluminal device includes one or more arrays of impelling mechanisms. For example an intraluminal device may include an array of impelling mechanisms aligned along an x-axis and a second array of impelling mechanisms aligned along a y-axis.

Figure 9:
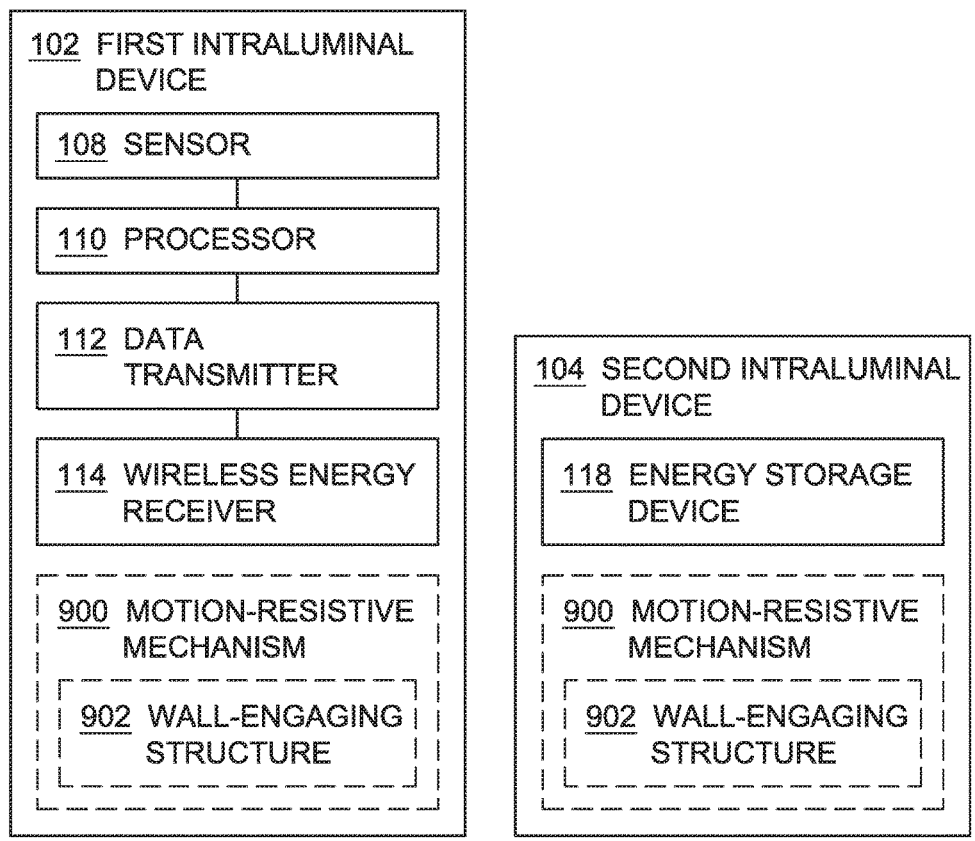
FIG. 9 is a schematic of an embodiment of a system such as shown in FIG. 1.

In an embodiment, shown in FIG. 9, at least one of the first intraluminal device 102 or the second intraluminal device 104 includes a motion-resistive mechanism 900. For example, the motion-resistive mechanism 900 is operable to resist a motion of the intraluminal device, such as to slow or stop the intraluminal device within the biological lumen. In an embodiment, the motion-resistive mechanism 900 includes a wall-engaging structure 902 configured to engage a wall of the biological lumen to secure at least one of the first intraluminal device 102 or the second intraluminal device 104 with respect to the wall of the biological lumen. For example, the wall-engaging structure 902 includes at a structural component configured to physically interact with (e.g., grasp, adhere to, etc.) the wall of the biological lumen to resist motion of the intraluminal device, such as to anchor the intraluminal device, at least temporarily, with respect to the wall of the biological lumen. In an embodiment, the processor 110 is configured to direct the motion-resistive mechanism 900 proximate a wall of the biological lumen to secure the first intraluminal device with respect to the wall of the biological lumen. For example, the processor 110 can generate one or more control signals (e.g., after analysis of signals or lack of signals from the sensor 108) to control operation of the motion-resistive mechanism 900 to resist motion of one or more of the first intraluminal device 102 or the second intraluminal device 104 (e.g., via transmission of the control signals to the second intraluminal device 104). In an embodiment, the processor 110 is configured to direct the motion-resistive mechanism 900 proximate a wall of the biological lumen to secure the first intraluminal device 102 with respect to the wall of the biological lumen until the second intraluminal device 104 is within a threshold proximity of the first intraluminal device 102. For example, the processor 110 can generate one or more control signals to control operation of the motion-resistive mechanism 900 to stop motion of the first intraluminal device to permit time for the second intraluminal device 104 to move closer to the first intraluminal device 102 (e.g., permit time to "catch up," such as if the second intraluminal device 104 is introduced to the biological lumen at a time subsequent to introduction of the first intraluminal device 102 to the biological lumen). The processor 110 can make determinations as to the proximity of the respective intraluminal devices via sense signals received from one or more sensors of the system 100 (e.g., sensor 108, sensor 300, etc.). The processor 110 can initiate engagement of the motion-resistive mechanism 900 according to any of the protocols described herein, including but not limited to, sensing of a particular environmental condition (e.g., pH, temperature, pressure, etc.), distance between the respective intraluminal devices, orientation of the respective intraluminal devices, passage of a period of time, external control signal, or the like.

Figure 10:
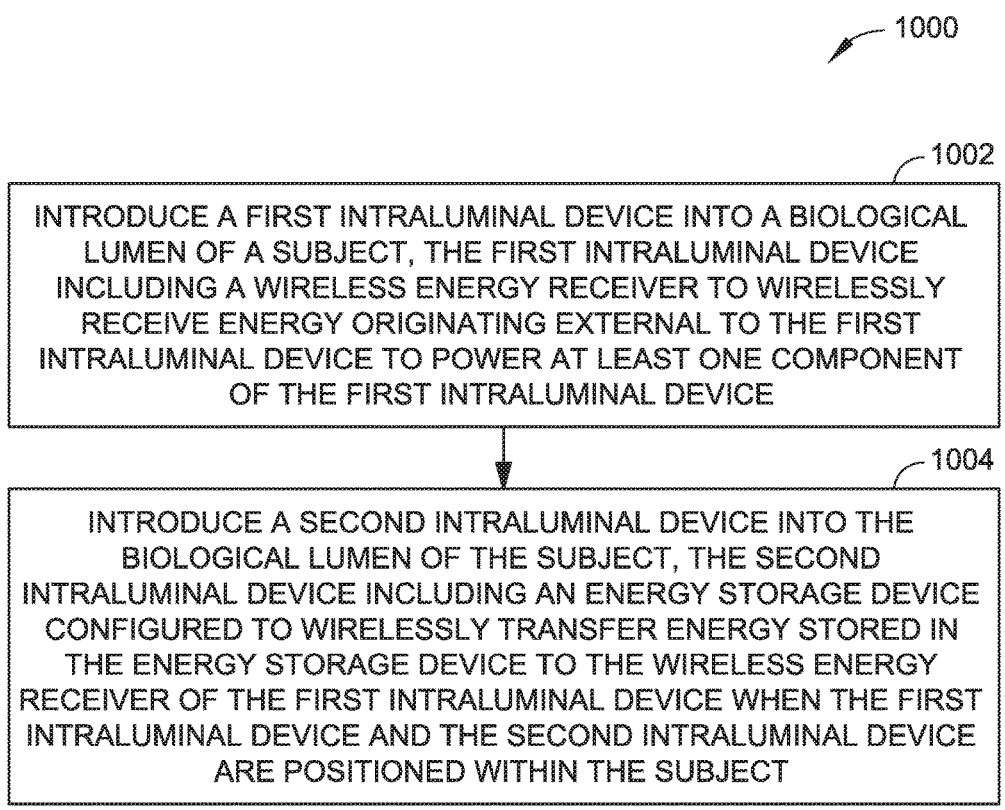
FIG. 10 is a flowchart of a method for intraluminal analysis in accordance with an example embodiment.

FIG. 10 illustrates a method 1000 for intraluminal analysis including transfer of energy from one intraluminal device to another intraluminal device. Method 1000 shows introducing a first intraluminal device into a biological lumen of a subject in block 1002, where the first intraluminal device includes a wireless energy receiver to wirelessly receive energy originating external to the first intraluminal device to power at least one component of the first intraluminal device. For example, the first intraluminal device 102 can be introduced to a biological lumen of a subject through one or more methods including, but not limited to, ingestion (e.g., for analysis of gastrointestinal systems), injection (e.g., for analysis of a respiratory system, a cardiovascular system, etc.), a cut down procedure, via an endoscope, via a catheter, via a trocar, or the like. Method 1000 also includes introducing a second intraluminal device into the biological lumen of the subject in block 1004, where the second intraluminal device includes an energy storage device configured to wirelessly transfer energy stored in the energy storage device to the wireless energy receiver of the first intraluminal device when the first intraluminal device and the second intraluminal device are positioned within the subject. For example, the second intraluminal device 104 can be introduced to the biological lumen of the subject through one or more methods including, but not limited to, ingestion (e.g., for analysis of gastrointestinal systems), injection (e.g., for analysis of a respiratory system, a cardiovascular system, etc.), a cut down procedure, via an endoscope, via a catheter, via a trocar, or the like. In an embodiment, the second intraluminal device 104 can be introduced to the same biological lumen as the first intraluminal device 102, or can be introduced to a different biological lumen than the first intraluminal device 102 (e.g., a biological lumen of a different body system, a different biological lumen within the same body system as the biological lumen into which the first intraluminal device 102 was introduced, etc.). In an embodiment, the second intraluminal device 104 can be introduced to the biological lumen substantially simultaneously with the first intraluminal device 102 (e.g., simultaneous introduction may be limited by biological factors, such as the size of the biological lumen, may be limited by the introduction method, etc., whereby substantially simultaneously can refer to substantially co-introduced to the biological lumen as dictated by any physical limitation of the biological lumen or the intraluminal devices preventing precise simultaneous introduction), can be introduced prior to introduction of the first intraluminal device 102, or can be introduced subsequent to introduction of the first intraluminal device 102.

Figure 11:
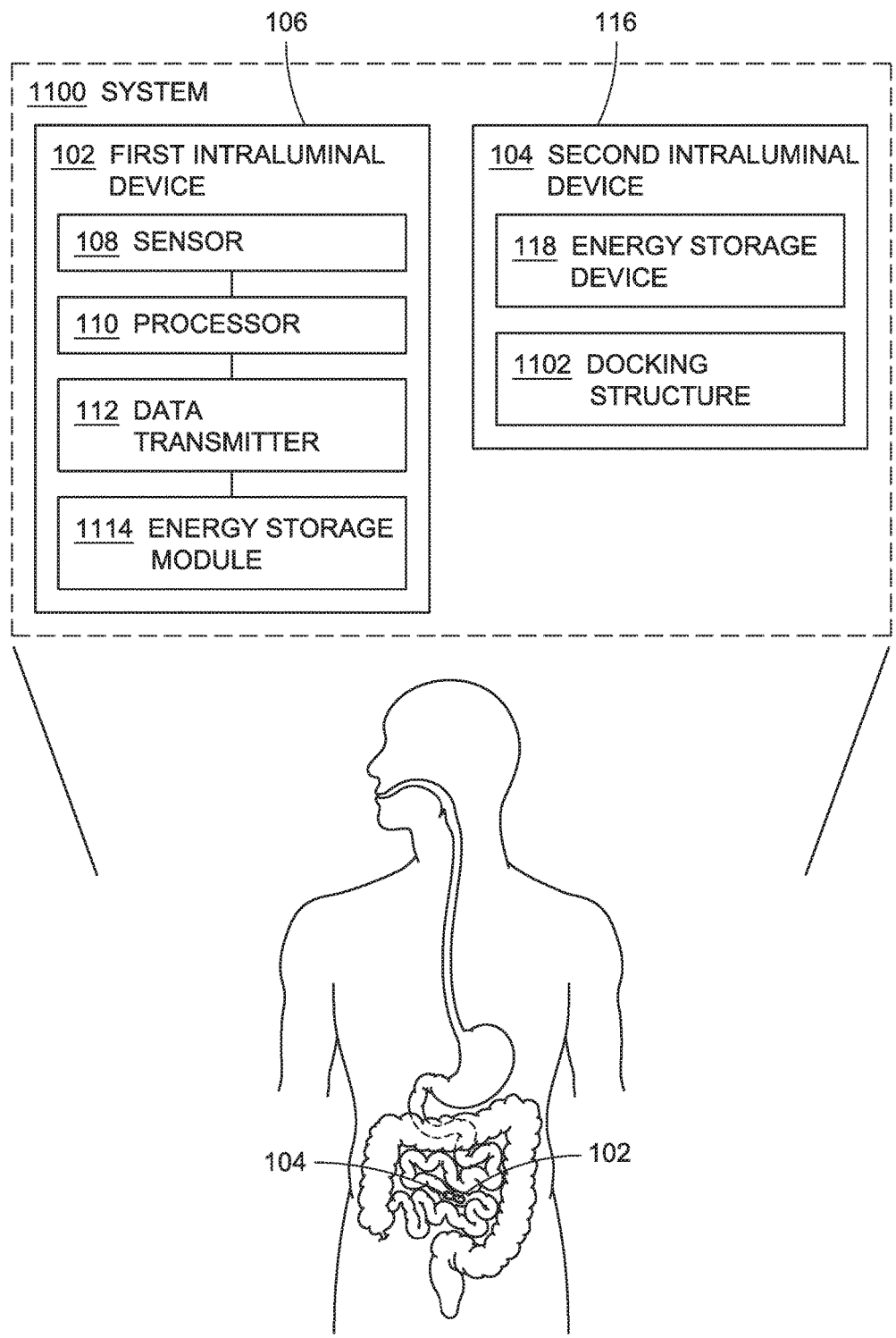
FIG. 11 is a schematic of a system for modular intraluminal device power transfer.

In an embodiment, shown in FIG. 11, a system (or device) 1100 is configured to provide wireless power or energy transfer between modular intraluminal devices when the intraluminal devices are positioned within one or more biological lumens of an individual subject (e.g., a human subject, an animal subject). The system 1100 includes the first intraluminal device 102 and the second intraluminal device 104, each of which is configured for deployment within one or more biological lumens within the individual subject, such as a lumen of the gastrointestinal tract shown in FIG. 11. Certain components and/or functionalities of the first intraluminal device 102 and the second intraluminal device 104 of system 1100 can be the same as or similar to those described regarding system 100 with reference to FIGS. 1-9, such as, for example, the structure and/or functionalities associated with body structure 106, the sensor 108, the processor 110, the data transmitter 114, the second body structure 116, the energy storage device 118, the power transmitter 200, the sensor 300, the circuitry 302, the receiver 304, the location determination device 400, the actuator 600, the control circuit 614, the motive structure 700, the steering mechanism 800, the motion-resistive mechanism 900, and/or other component. For system 1100, the first intraluminal device 102 includes an energy storage module 1114 configured to power at least one of the sensor 108, the processor 110, or the data transmitter 112. The energy storage module 1114 is configured to receive energy from the second intraluminal device 104, which can occur via wireless mechanisms or physical connections, as described herein. The energy storage device 118 is coupled to the second body structure 116 of the second intraluminal device 104 and is configured to transfer energy stored in the energy storage device 118 to the energy storage module 1114 of the first intraluminal device 102, where such energy transfer can depend upon coupling between the first intraluminal device 102 and the second intraluminal device 104 within the biological lumen. For example, the second intraluminal device 104 can include a docking structure 1102 coupled to the second body structure 116. The docking structure 1102 is configured to couple (e.g., conditionally couple, where such coupling is a temporary coupling based on satisfaction of a coupling condition, including, but not limited to, power supply, time, environmental conditions, etc.) the first intraluminal device 102 with the second intraluminal device 104, where the energy storage device 118 is configured to transfer the energy stored in the energy storage device 118 to the energy storage module 1114 when the first intraluminal device 102 and the second intraluminal device 104 are coupled via the docking structure 1102. The docking structure 1102 is operable to automatically decouple the first intraluminal device 102 and the second intraluminal device 104 subsequent to transfer of the energy from the energy storage device 118 of the second intraluminal device 104 to the energy storage module 1114 of the first intraluminal device 102. For example, the coupling between the first intraluminal device 102 and the second intraluminal device 104 provided by the docking structure 1102 can be maintained while power is supplied to or through the docking structure 1102, where the power can be provided on a finite or temporary basis by the energy storage device 118 during transfer of energy to the energy storage module 1114. When energy transfer is complete, or where the energy storage device 118 no longer has sufficient energy stored, the power supplied to or through the docking structure 1102 can cease, thereby severing the coupling between the first intraluminal device 102 and the second intraluminal device 104.

Figure 12:
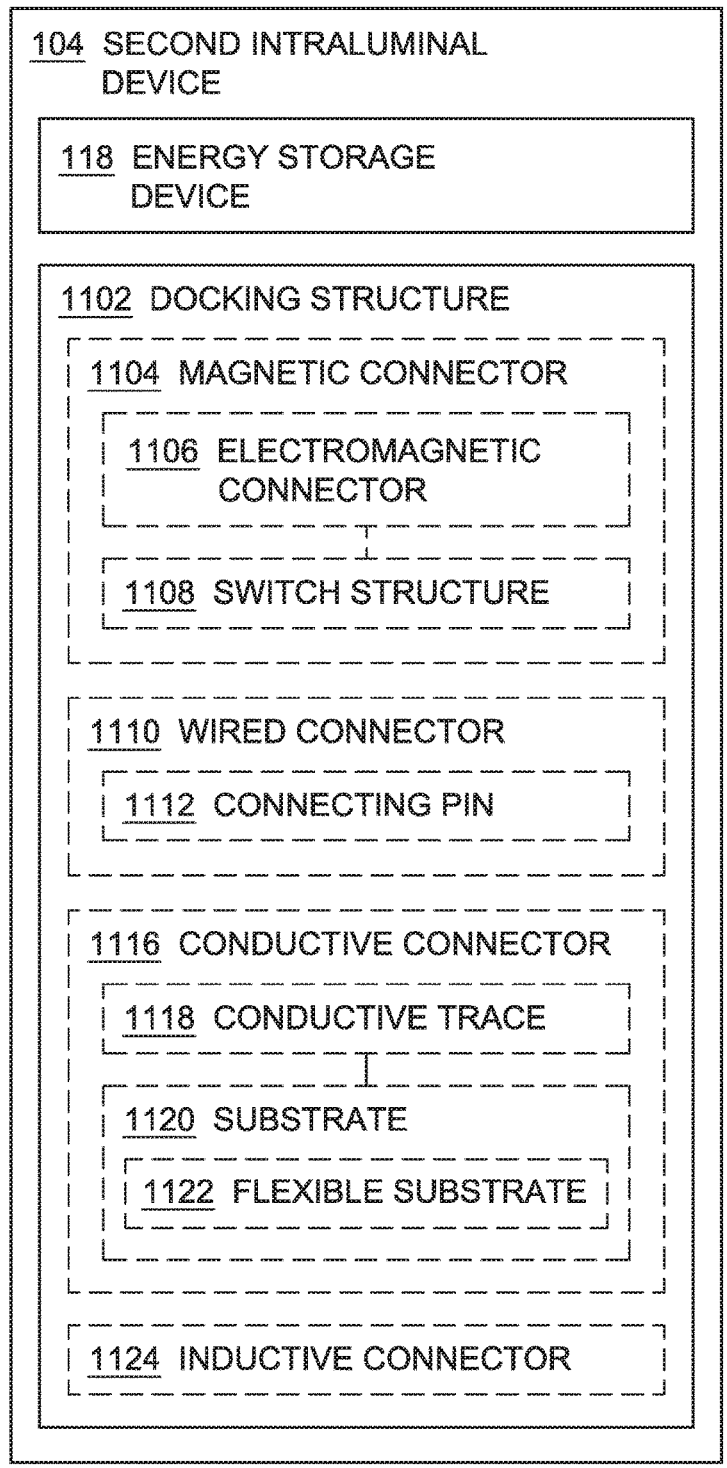
FIG. 12 is a schematic of an embodiment of a system such as shown in FIG. 11.

In an embodiment, shown in FIG. 12, the docking structure 1102 includes, but is not limited to, one or more of a magnetic connector 1104, an electromagnetic connector 1106, a switch structure 1108, a wired connector 1110, a connecting pin 1112, a conductive connector 1116, a conductive trace 1118, a substrate 1120, a flexible substrate 1122, or an inductive connector 1124. For example, the magnetic connector 1104 can include one or more of a diamagnetic material, a paramagnetic material, a ferromagnetic material, etc. operable to magnetically couple the first intraluminal device 102 with the second intraluminal device 104. In an embodiment, the magnetic connector 1104 includes an electromagnetic connector 1106 configured to provide an electromagnetic connection between the first intraluminal device 102 and the second intraluminal device 104, such as while supplied with energy (e.g., electric current, etc.). For example, the energy storage device 118 of the second intraluminal device 104 can power the electromagnetic connection established by the electromagnetic connector 1106 between the first intraluminal device 102 and the second intraluminal device 104. In an embodiment, the electromagnetic connection can be maintained until loss of power of the energy storage device 118 of the second intraluminal device 104. In an embodiment, the electromagnetic connection can be maintained until a power level of the energy storage device 118 of the second intraluminal device 104 is reduced below a threshold power level. In an embodiment, the docking structure 1102 includes a switch structure 1108 configured to maintain the electromagnetic connection until a power level of the energy storage device 118 of the second intraluminal device 104 is reduced below a threshold power level. For example, the switch structure 1108 can automatically cease powering the electromagnetic connector 1106 upon activation or deactivation of the switch to decouple the electromagnetic connection (such as by providing a break in an electrical circuit powering the electromagnetic connector 1106). In an embodiment, the magnetic connector 1104 includes a flux that is suitable to provide conditional coupling between the first intraluminal device 102 and the second intraluminal device 104 and that does not provide substantial coupling between the first intraluminal device 102 and the second intraluminal device 104 across biological tissue of the individual subject. For instance, avoiding coupling across biological tissue can prevent or avoid conditions for volvulus, bowel perforation, tissue ulcerations, or the like. For example, each magnet associated with the magnetic connector 1104 can have a flux index of about 50 $kG^2 \, mm^2$ or less.

In an embodiment, the docking structure 1102 includes the wired connector 1110 to provide a physical coupling between the first intraluminal device 102 and the second intraluminal device 104. For example, the wired connector 1110 can include one or more connecting pins 1112 to connect the first intraluminal device 102 to the second intraluminal device 104 within the biological lumen. In an embodiment, the docking structure 1102 includes the conductive connector 1116 to provide a physical coupling and electrical coupling between the first intraluminal device 102 and the second intraluminal device 104. For example, the conductive connector 1116 can include the conductive trace 1118, where the conductive trace can be disposed on the substrate 1120 (e.g., the flexible substrate 1122) to provide the coupling between the first intraluminal device 102 and the second intraluminal device 104. In an embodiment, the docking structure 1102 includes the inductive connector 1124 to provide an inductive/electrical coupling between the first intraluminal device 102 and the second intraluminal device 104. For example, inductive connector 1124 can be included in addition to one or more physical connectors between the first intraluminal device 102 and the second intraluminal device 104, such as to provide physical coupling and inductive/electrical coupling between the first intraluminal device 102 and the second intraluminal device 104.

Figure 13:
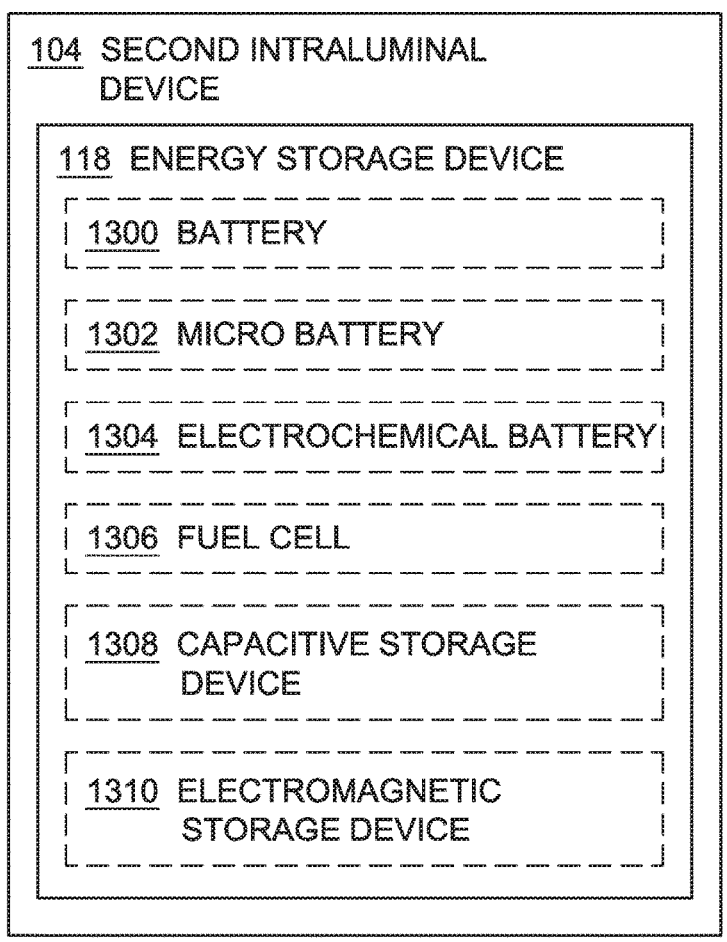
FIG. 13 is a schematic of an embodiment of a system such as shown in FIG. 11.

In an embodiment, an example of which is shown in FIG. 13, at least one of the energy storage device 118 and the energy storage module 1114 includes, but is not limited to, a battery 1300, a microbattery 1302, an electrochemical battery 1304, a fuel cell 1306, a capacitive energy storage device 1308, or an electromagnetic storage device 1310.

Figure 14:
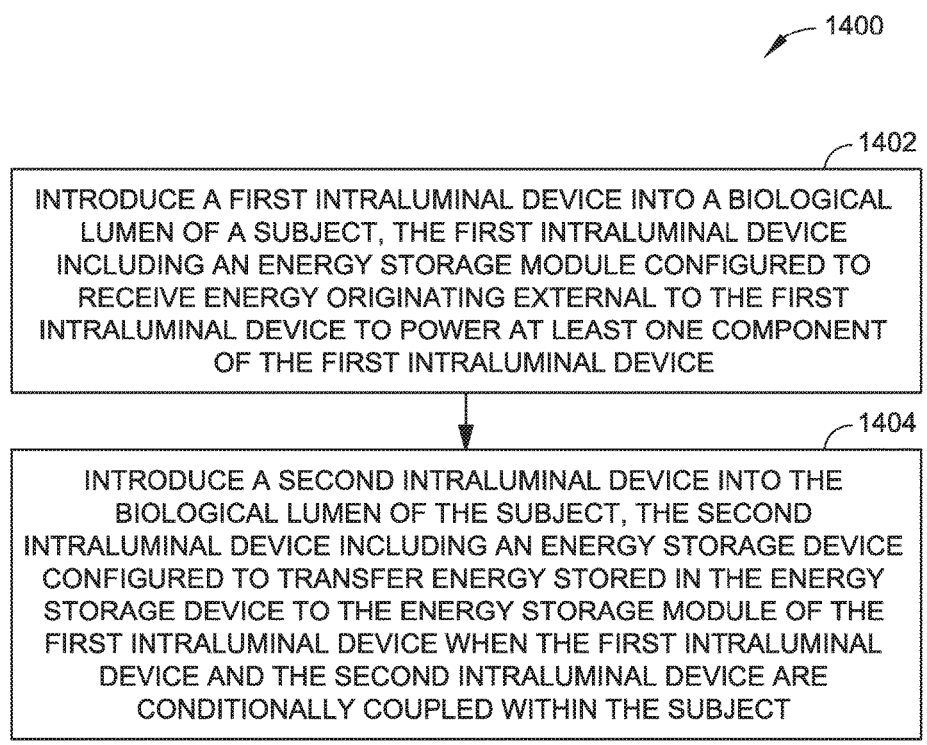
FIG. 14 is a flowchart of a method for intraluminal analysis in accordance with an example embodiment.

FIG. 14 illustrates a method 1400 for intraluminal analysis including transfer of energy from one intraluminal device to another intraluminal device. Method 1400 shows introducing a first intraluminal device into a biological lumen of a subject in block 1402, where the first intraluminal device includes an energy storage module configured to receive energy originating external to the first intraluminal device to power at least one component of the first intraluminal device. For example, the first intraluminal device 102 can be introduced to a biological lumen of a subject through one or more methods including, but not limited to, ingestion (e.g., for analysis of gastrointestinal systems), injection (e.g., for analysis of a respiratory system, a cardiovascular system, etc.), a cut down procedure, via an endoscope, via a catheter, via a trocar, or the like. Method 1400 also includes introducing a second intraluminal device into the biological lumen of the subject in block 1404, where the second intraluminal device includes an energy storage device configured to transfer energy stored in the energy storage device to the energy storage module of the first intraluminal device when the first intraluminal device and the second intraluminal device are conditionally coupled within the subject.

For example, the second intraluminal device 104 can be introduced to the biological lumen of the subject through one or more methods including, but not limited to, ingestion (e.g., for analysis of gastrointestinal systems), injection (e.g., for analysis of a respiratory system, a cardiovascular system, etc.), a cut down procedure, via an endoscope, via a catheter, via a trocar, or the like. In an embodiment, the second intraluminal device 104 can be introduced to the same biological lumen as the first intraluminal device 102, or can be introduced to a different biological lumen than the first intraluminal device 102 (e.g., a biological lumen of a different body system, a different biological lumen within the same body system as the biological lumen into which the first intraluminal device 102 was introduced, etc.). In an embodiment, the second intraluminal device 104 can be introduced to the biological lumen substantially simultaneously with the first intraluminal device 102 (e.g., simultaneous introduction may be limited by biological factors, such as the size of the biological lumen, may be limited by the introduction method, etc., whereby substantially simultaneously can refer to substantially co-introduced to the biological lumen as dictated by any physical limitation of the biological lumen or the intraluminal devices preventing precise simultaneous introduction), can be introduced prior to introduction of the first intraluminal device 102, or can be introduced subsequent to introduction of the first intraluminal device 102. In an embodiment, the conditional coupling between the first intraluminal device 102 and the second intraluminal device 104 can be facilitated by the docking structure 1102, which can provide conditional coupling on the basis of electromagnetic connections, wired connections, magnetic connections, or the like. For example, the condition for coupling can include a power level threshold for one or more of the energy storage device 118 or the energy storage module 1114, where upon exceeding or falling below the power level threshold, the docking structure 1102 ceases to provide a coupling between the first intraluminal device 102 and the second intraluminal device 104.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of one or more of the systems described herein (e.g., system 100, system 1100, etc.) used to provide power transfer between modular intraluminal devices, and any associated computing devices of the system operate as specific use computers for purposes of the claimed system, and not general use computers. In an embodiment, at least one associated computing device of the system operates as a specific use computer for purposes of the claimed system, and not a general use computer. In an embodiment, at least one of the associated computing devices of the system is hardwired with a specific ROM to instruct the at least one computing device. In an embodiment, one of skill in the art recognizes that the systems described herein (e.g., system 100, system 1100, etc.) and associated systems/devices effect an improvement at least in the technological field of intraluminal device power transfer.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An intraluminal traveling modular system, comprising:
    a first intraluminal device, the first intraluminal device including
        a body structure dimensioned and structured to travel through a biological lumen of a subject;
        a sensor coupled to the body structure, the sensor oriented to detect at least one characteristic of the biological lumen and to generate one or more sense signals in response thereto;
        a processor operably coupled to the sensor, the processor configured to receive the one or more sense signals;
        a data transmitter coupled to the body structure and configured to wirelessly transmit one or more data signals associated with the one or more sense signals responsive to instruction by the processor; and
        an energy storage module configured to power at least one of the sensor, the processor, or the data transmitter; and
    a second intraluminal device, the second intraluminal device including
        a second body structure dimensioned and structured to travel through the biological lumen of the subject;
        an energy storage device coupled to the second body structure, the energy storage device configured to transfer energy stored in the energy storage device to the energy storage module of the first intraluminal device; and
        a docking structure coupled to the second body structure, the docking structure configured to couple the first intraluminal device with the second intraluminal device, the energy storage device configured to transfer the energy when the first intraluminal device and the second intraluminal device are coupled via the docking structure, the docking structure further configured to automatically decouple the first intraluminal device and the second intraluminal device subsequent to transfer of the energy from the energy storage device of the second intraluminal device to the energy storage module of the first intraluminal device,
    wherein the first intraluminal device further includes
        a wall-engaging structure capable of engaging a wall of the biological lumen to secure the first intraluminal device with respect to the wall of the biological lumen; and
        a second sensor configured to measure a proximity between the first intraluminal device and the second intraluminal device, and
    wherein the processor is configured to direct the wall-engaging structure to secure the first intraluminal device with respect to the wall of the biological lumen until the measured proximity between the first intraluminal device and the second intraluminal device is within a threshold proximity.

2. The intraluminal traveling modular system of claim 1, wherein the docking structure includes a magnetic connector configured to couple the first intraluminal device with the second intraluminal device.

3. The intraluminal traveling modular system of claim 2, wherein the magnetic connector includes an electromagnetic connector configured to establish an electromagnetic connection between the first intraluminal device and the second intraluminal device.

4. The intraluminal traveling modular system of claim 3, wherein the energy storage device of the second intraluminal device is configured to power the electromagnetic connection.

5. The intraluminal traveling modular system of claim 4, wherein the electromagnetic connection is maintained until loss of power of the energy storage device of the second intraluminal device.

6. The intraluminal traveling modular system of claim 4, wherein the electromagnetic connection is maintained until a power level of the energy storage device of the second intraluminal device is reduced below a threshold power level.

7. The intraluminal traveling modular system of claim 4, wherein the docking structure includes a switch structure to maintain the electromagnetic connection until a power level of the energy storage device of the second intraluminal device is reduced below a threshold power level.

8. The intraluminal traveling modular system of claim 1, wherein at least one of the first intraluminal device or the second intraluminal device further includes a motive structure.

9. The intraluminal traveling modular system of claim 1, wherein the processor is configured to direct the wall-engaging structure to secure the first intraluminal device with respect to the wall of the biological lumen when a power level of the first intraluminal device is below a threshold power value.

10. The intraluminal traveling modular system of claim 1, further including:
    a location determination device, the location determination device configured to determine at least one of an absolute location or a relative location of at least one of the first intraluminal device or the second intraluminal device.

11. The intraluminal traveling modular system of claim 10, wherein the location determination device includes at least one of a physical sensor, a chemical sensing device, an optical sensor, a radio frequency device, an acoustic device, a localization beacon, or a magnetic tracking system.

12. The intraluminal traveling modular system of claim 1, wherein at least one of the first intraluminal device or the second intraluminal device includes an actuator configured to initiate transfer of energy from the energy storage device of the second intraluminal device to the energy storage module of the first intraluminal device.

13. The intraluminal traveling modular system of claim 12, further including:
   a control circuit coupled to the actuator, the control circuit driving the actuator in response to at least one of: a timer output, a sensor output, or a communication received from a source external to the biological lumen of the subject.

14. The intraluminal traveling modular system of claim 1, wherein the energy storage device includes at least one of a battery, a microbattery, an electrochemical battery, a fuel cell, a capacitive storage device, or an electromagnetic storage device.

* * * * *